(12) United States Patent
Zhu et al.

(10) Patent No.: US 9,206,405 B2
(45) Date of Patent: Dec. 8, 2015

(54) GLYCOSYL HYDROLASE WITH BETA-XYLOSIDASE AND BETA-GLUCOSIDASE ACTIVITIES AND USES THEREOF

(75) Inventors: Ping Zhu, Beijing (CN); Haili Cheng, Beijing (CN); Ruiyu Zhao, Beijing (CN); Kedi Cheng, Beijing (CN); Huixia He, Beijing (CN); Chao Meng, Beijing (CN); Huixin Zhu, Beijing (CN)

(73) Assignee: Institute of Materia Medica, Chinese Academy of Medical Sciences, Beijing (CN)

(*) Notice: Subject to any disclaimer, the term of this patent is extended or adjusted under 35 U.S.C. 154(b) by 220 days.

(21) Appl. No.: 13/806,439

(22) PCT Filed: Apr. 12, 2011

(86) PCT No.: PCT/CN2011/072678
§ 371 (c)(1),
(2), (4) Date: Jan. 24, 2013

(87) PCT Pub. No.: WO2011/160484
PCT Pub. Date: Dec. 29, 2011

(65) Prior Publication Data
US 2013/0130330 A1 May 23, 2013

(30) Foreign Application Priority Data

Jun. 25, 2010 (CN) .......................... 2010 1 0209089

(51) Int. Cl.
| | |
|---|---|
| *C12P 19/02* | (2006.01) |
| *C12P 19/14* | (2006.01) |
| *C12N 9/24* | (2006.01) |
| *C12N 1/19* | (2006.01) |
| *C12N 9/42* | (2006.01) |
| *C12P 17/02* | (2006.01) |

(52) U.S. Cl.
CPC .............. *C12N 9/2402* (2013.01); *C12N 9/248* (2013.01); *C12N 9/2434* (2013.01); *C12N 9/2445* (2013.01); *C12P 17/02* (2013.01); *C12P 19/14* (2013.01); *C12Y 302/01021* (2013.01); *C12Y 302/01037* (2013.01)

(58) Field of Classification Search
None
See application file for complete search history.

(56) References Cited

U.S. PATENT DOCUMENTS

| | | | |
|---|---|---|---|
| 4,814,470 A | 3/1989 | Colin et al. | |
| 5,700,669 A | 12/1997 | Hanson et al. | |
| 6,028,206 A | 2/2000 | Chattopadhyay et al. | |
| 7,413,888 B2 * | 8/2008 | Fidantsef et al. | 435/209 |

FOREIGN PATENT DOCUMENTS

| | | |
|---|---|---|
| CN | 100998373 A | 7/2007 |
| CN | 101054561 A | 10/2007 |
| CN | 101381708 A | 3/2009 |
| CN | 101492661 A | 7/2009 |
| CN | 101701196 A | 5/2010 |
| EP | 0 668 360 B1 | 4/1999 |
| EP | 0 905 130 B1 | 3/2002 |
| EP | 1 298 128 B1 | 3/2005 |

OTHER PUBLICATIONS

Henrissat, B., Biochem. J. 280:309-316, 1991.*
Harlow, E., "Antibodies a Laboratory Manual", Cold Spring Harbor Laboratory, 1988, p. 76.*
Kwok, S., "The Lignocellulolytic System in *Lentinula edodes*", Thesis, The Chinese University of Hong Kong, 2009.*
Belfaquih, N. et al., "A bifunctional β-xylosidase-xylose isomerase from *Streptomyces* sp. EC 10" *Enzyme Microb Technol.* (2000) pp. 114-121, vol. 27.
Denis, J.N. et al., "A Highly Efficient, Practical Approach to Natural Taxol" *J Am Chem Soc.* (1988) pp. 5917-5919, vol. 110, No. 17.
Gargouri, M. et al., "Fungus β-glycosidases: immobilization and use in alkyl-β-glycoside synthesis" *Journal of Molecular Catalysis: B: Enzymatic* (2004) pp. 89-94, vol. 29, Nos. 1-6.
Golubev, A.M. et al., "Purification, Crystallization and Preliminary X-ray Study of β-xylosidase from *Trichoderma reesei*" *Acta Crystallographica Secion D Biological Crystallography* (2000) pp. 1058-1060, vol. 56(Pt 8).
Hao, D.C. et al., "Bacterial Diversity of *Taxus* rhizosphere: Culture-Independent and Culture-Dependent Approaches" *FEMS Microbiol Lett* (2008) pp. 204-212, vol. 284.
Horwitz, S.B. "Taxol (paclitaxel): Mechanisms of Action" *Ann Oncol.* (1994) pp. S3-S6, vol. 5, Suppl. 6.
Horwitz, S.B., "How to Make Taxol from Scratch" *Nature* (1994) pp. 593-594, vol. 367.
Kingston, D.G.I. et al., "The Taxane Diterpenoids. In: Herz W, et al. eds. Progress in the chemistry of organic natural products" *New York: Springer-Verlag* (1993) pp. 161-165.
Kitamoto, N. et al., "Sequence Analysis, Overexpression, and Antisense Inhibition of a β-xylosidase Gene, xylA, from *Aspergillus oryzae* KBN616" *Applied and Environmental Microbiology* (Jan. 1999) pp. 20-24, vol. 65, No. 1.
Kurakake, M. et al., "Characteristics of transxylosylation by β-xylosidase from *Aspergillus awamori* K4" *Biochimica et Biophysica Acta* (2005) pp. 272-279, vol. 1726, No. 3.

(Continued)

Primary Examiner — David J Steadman

(74) Attorney, Agent, or Firm — Scully, Scott, Murphy & Presser, P.C.

(57) ABSTRACT

A novel glycosyl hydrolase with activities of beta-xylosidase and beta-glucosidase is provided. Said glycosyl hydrolase can convert 7-xylosyltaxane compounds to 7-hydroxyltaxane compounds.

15 Claims, 5 Drawing Sheets

(56) References Cited

OTHER PUBLICATIONS

Lama, L. et al., "Purification and Characterization of Thermostable xylanase and β-xylosidase by the Thermophilic Bacterium *Bacillus thermantarcticus*" *Research in Microbiology* (2004) pp. 283-289, vol. 155, No. 4.

Margolles-Clark, E. et al., "Cloning of Genes Encoding α-L-Arabinofuranosidase and β-Xylosidase from *Trichoderma reesei* by Expression in *Saccharomyces cerevisiae*" *Applied and Environmental Microbiology* (Oct. 1996) pp. 3840-3846, vol. 62, No. 10.

Pan, I.H. et al., "Effective Extraction and Purification of β-xylosidase from *Trichoderma koningii* Fermentation Culture by Aqueous Two-Phase Partitioning" *Enzyme and Microbiology Technology* (2001) pp. 196-201, vol. 28, Nos. 2-3.

Pérez-González, J.A. et al., "Molecular Cloning and Transcriptional Regulation of the *Aspergillus nidulans xlnD* Gene Encoding a β-Xylosidase" *Applied and Environmental Microbiology* (Apr. 1998) pp. 1412-1419, vol. 64, No. 4.

Rao, K.V., "Taxol and Related Taxanes.I. Taxanes of *Taxus brevifolia* Bark" *Pharmaceutical Research* (1993) pp. 521-524, vol. 10, No. 4.

Reen, F.J. et al., "Molecular Characterisation and Expression Analysis of the First Hemicellulase Gene (bxl1) Encoding β-xylosidase From the Thermophilic Fungus *Talaromyces emersonii*" *Biochemical and Biophysical Research Communication* (2003) pp. 579-585, vol. 305, No. 3.

Ringel, I. et al., "Studies with RP 56976 (Taxotere): A Semisynthetic Analogue of Taxol" *Journal of the National Cancer Institute* (Feb. 1991) pp. 288-291, vol. 83, No. 4.

Saha, B.C., "Purification and Characterization of an Extracellular β-xylosidase From a Newly Isolated *Fusarium verticillioides*" *Journal of Industrial Microbiology & Biotechnology* (2001) pp. 241-245, vol. 27, No. 4.

Sénilh, V. et al. "Mise en evidence de nouveaux analogues du taxol extraits de *Taxus baccata*" *Journal of Natural Products* (Jan.-Feb. 1984) pp. 131-137, vol. 47, No. 1.

Tuohy, M.G. et al., "The xylan-Degrading Enzyme System of *Talaromyces emerconii:* Novel enzymes with Activity Against aryl-β-D-xylosides and Unsubstituted xylans" *Journal of Biochem.* (1993) pp. 515-523, vol. 290.

Van Peij, N.N. et al., "β-Xylosidase Activity, Encoded by xlnD, is Essential for Complete Hydrolysis of xylan by *Aspergillus niger* But Not for Induction of the xylanolytic Enzyme Spectrum" *Eur J Biochem.* (1997) pp. 164-173, vol. 245, No. 1.

Wakiyama, M. et al., "Purification and Properties of an Extracellular β-Xylosidase From *Aspergillus japonicus* and Sequence analysis of the Encoding Gene" *Journal of Bioscience and Bioengineering* (2008) pp. 398-404, vol. 106, No. 4.

GenBank Accession No. XP_760179, "Direct Submission" dated Apr. 25, 2006, retrieved on Jul. 4, 2011 from GenBankDatabase.

GenBank Accession No. XM_755086, "The genome sequence of *Ustilago maydis*" dated Apr. 25, 2006, retrieved on Jul. 4, 2011 from GenBankDatabase.

Jiang, T.Y., "Studies on the construction of the P450 reductase gene replacement vector for the optimization of the engineered artemisinin producing yeast" *Chinese Master's Theses Full-text Database Basic Sciences* (Jul. 15, 2009) pp. 50-54, vol. 7.

International Search Report dated Jul. 21, 2011 issued in International Application No. PCT/CN2011/072678.

\* cited by examiner

GLYCOSYL HYDROLASE WITH BETA-XYLOSIDASE AND BETA-GLUCOSIDASE ACTIVITIES AND USES THEREOF

TECHNICAL FIELD

The present invention relates to a novel glycosyl hydrolase (GH, also called glycoside hydrolase or glycosidase), the amino acid sequence of said enzyme and the nucleotide sequence encoding the enzyme. Particularly, the enzyme has both β-xylosidase and β-glucosidase activities, and can specifically remove the xylosyl group from 7-xylosyltaxane compounds by hydrolysis. The invention relates to the nucleotide sequence encoding said glycosyl hydrolase of 7-xylosyltaxanes, the amino acid sequence of said enzyme and/or the use of the glycosyl hydrolase-producing strains.

BACKGROUND

Paclitaxel (Taxol') is mainly produced by species of *Taxus*. As one of the important achievements in anticancer drug research of 1990's, it has attracted worldwide attention since its advent because of its unique anti-tumor mechanism and prominent anti-tumor activities (Kingston DGI, et al. The taxane diterpenoids. In: Herz W, et al. eds. *Progress in the chemistry of organic natural products*. New York: Springer-Verlag, 1993, 161-165). It can bind to tubulins, promote the polymerization of tubulins and inhibit the depolymerization thereof, and then hinder the formation of the spindles during the mitosis of cells, such that the cells are stalled in the G2/M phase (Horwitz S B. Taxol (paclitaxel): mechanisms of action. *Ann Oncol*. 1994, 5 Suppl.). Currently the paclitaxel has been clinically used as a first-line drug for the treatment of breast, ovarian and non-small cell lung cancers, etc. It is also effective against head and neck cancers, melanoma, colon cancer and HIV-induced Kaposi's sarcoma.

The content of paclitaxel in *Taxus* plants is extremely low and it is mainly present in the bark, which portion has the highest content of paclitaxel, at only about 0.02% (U.S. Pat. No. 6,028,206). A 100-year-old *Taxus* tree might yield 3 kg of bark which may provide about 300 mg paclitaxel (Horwitz, S B. How to make taxol from scratch. *Nature* 1994, 367: 593-594). Thus, to harvest 1 kg of paclitaxel from barks needs about 3,000 trees, and 3~4 one-hundred year old trees are cut down to meet the requirement of one patient's dose. In an alternative method, 10-deacetylbaccatin III with a higher content (up to about 0.1%) is extracted from the leaves of *Taxus baccata* L., etc, and used as the material for semi-synthesis of paclitaxel and its structural analog, taxotere, which is slightly more active and more soluble in water than paclitaxel (Denis J N, et al. A highly efficient, practical approach to natural taxol. *J Am Chem Soc*. 1988, 110(17): 5917-5919; Horwitz RI. Studies with RP 56976 (Taxotere): A semisynthetic analogue of taxol. *J Nat Cancer Inst*. 1991, 83(4):288-291; U.S. Pat. No. 4,814,470). The nursery culture of the shrub yew hybrid species is also believed to be the simplest, renewable and the lowest cost way to obtain paclitaxel.

In addition to the very little content of paclitaxel, C-7 xylosyltaxane compounds (taxane-xyloside) having a mother nucleus structure of paclitaxel, including 7-beta-xylosyl-10-deacytyltaxol (XDT), 7-beta-xylosyl-10-deacetylcephalomannine (XDC), and 7-beta-xylosyl-10-deacytyltaxol C (XDTC), etc, have been isolated from yew bark, wherein 7-beta-xylosyl-10-deacytyltaxol (XDT) is most abundant (Senilh V, et al. Mise en evidence de nouveaux analogues du taxol extraits de *Taxus baccata*. *J Nat Prod*. 1984, 47:131-137; Rao K V. Taxol and related taxanes. I. Taxanes of *Taxus brevifolia* bark. *Pharm Res*. 1993, 10:521-524). For example, XDT, XDC and XDTC could be obtained with the yields of 0.5%, 0.02% and 0.0075%, respectively (EP patent 0,905,130B1). These 7-xylosyltaxane compounds can be hydrolyzed by chemical approaches (U.S. Pat. No. 6,028,206; EP patent 1,298,128B1) or biological approaches (U.S. Pat. No. 5,700,669; CN patent No. 200610046296.6; CN patent No. 200710012698.9) to remove the xylosyl group and generate the corresponding 7-hydroxyltaxanes which can be used in chemical semi-synthesis of paclitaxel or taxotere to enhance the utilization of the source of yew trees and alleviate the imbalance between supply and demand of paclitaxel or its analogues. Comparatively speaking, the chemical approach has some disadvantages, such as relatively low yield, more complicated reaction process and environmental pollution, while the biological approach is more environmentally friendly.

U.S. Pat. No. 5,700,669A, EP patent 0,668,360B1 and relevant articles (Hanson R L, et al. Enzymatic hydrolysis of 7-xylosyltaxanes by xylosidase from *Moraxella* sp. *Biotechnol Appl Biochem* 1997, 26: 153-158) disclosed the hydrolyzing method by use of the bacteria *Moraxella* sp. (ATCC55475), *Bacillus macerans* (ATCC55476), *Bacillus circulans* (ATCC55477) and *Micrococcus* sp. (ATCC55478) to convert C-7 xylosyltaxanes into C-7 hydroxyltaxanes, among which the *Moraxella* sp. strain showed the highest conversion ability. Adding 0.5 mg 7-xylosyl-10-deacytyltaxol (XDT) to 2 ml of cell suspension (wet cells, 91.5 mg/ml; XDT, 0.25 mg/ml), the suspension was mixed end-over-end at 12 rpm for 21 h at 28° C. The reaction was then stopped with methanol and the sample was assayed by HPLC. No XDT was found to be remaining and the yield of 10-deacytyltaxol (DT) was 0.23 mg/ml.

CN patent (No. 200610046296.6) and relevant article (Hao D C, et al. Bacterial diversity of *Taxus rhizosphere*: culture-independent and culture-dependent approaches. *FEMS Microbiol Lett* 2008, 284:204-212) disclosed a hydrolyzing method to convert C-7 xylosyltaxanes to C-7 hydroxyltaxanes using *Leifsonia shinshuensis* DICP 16 (CCTCC No. M 206026). Similar culturing and converting conditions as those described in above-mentioned US patent is adopted, and 1 mg XDT was added to 2 ml cell suspension. After reacting at 100 rpm for 21 h at 30° C., the reaction was terminated with 2 ml methanol. No XDT was found to be remaining in the reaction solution by HPLC and 0.4 mg/ml DT was produced. In another experiment, different concentrations of 7-xylosyl-10-deacetylbaccatin III (0.5, 0.9, 1.95, 3.1, 4.4, 5.2, and 6.75 mg/ml) were respectively added into 2 ml reaction solution in which the concentration of wet cells was 231.58 mg. The reaction was conducted at 31° C. and 120 rpm for over 40 h. The yield of 10-deacetylbaccatin III reached its highest yield when the concentration of the substrate is 1.95 mg/ml (Hao DC, et al. Bacterial diversity of *Taxus rhizosphere*: culture-independent and culture-dependent approaches. *FEMS Microbiol Lett* 2008, 284:204-212).

Another CN patent No. 200710012698.9 disclosed the actinomycete strain *Cellulosimicrobium cellulans* (XZ-5CCTCC No. M 207130), the hydrolase and their use in the conversion of taxanes: 10 ml XDT (with a concentration of 5 mg/ml) was added into 90 ml crude enzyme solution (1 ml of the *Cellulosimicrobium cellulans* seed solution cultured at 30° C. for 2 days was introduced into 100 ml medium and cultured at 30° C., 150 rpm for 5 days, and the resultant was centrifuged and the supernatant was isolated to yield the so-called crude enzyme solution) and the reaction was conducted at 30° C. at 50 rpm for 20 h to yield 40 mg DT.

Overall, all the biological approaches mentioned above have potential application values in the hydrolysis of 7-xylosyltaxanes. However, the yields are not high enough to meet the requirement of the industrial mass production, due to the ubiquitous low amount of enzyme in the cells and low substrate solubility in water in the prior arts.

Several kinds of β-xylosidases have been isolated from fungi and other organisms (Tuohy M G, et al. The xylan-degrading enzyme system of *Talaromyces emersonii*: novel enzymes with activity against aryl beta-D-xylosides and unsubstituted xylans. *Biochem J.* 1993, 290 (Pt 2):515-523; Golubev A M, et al. Purification, crystallization and preliminary X-ray study of β-xylosidase from *Trichoderma reesei*. *Acta Crystallogr D Biol Crystallogr.* 2000, 56 (Pt 8):1058-1060; Pan I, et al. Effective extraction and purification of beta-xylosidase from *Trichoderma koningii* fermentation culture by aqueous two-phase partitioning. *Enzyme Microb Technol.* 2001, 28 (2-3):196-201; Rizzatti A C S, et al. Purification and properties of a thermostable extracellular β-D-xylosidase produced by a thermotolerant *Aspergillus phoenicis*. *J Ind Microbiol Biotechnol.* 2001, 26(3):156-160; Saha B C. Purification and characterization of an extracellular β-xylosidase from a newly isolated *Fusarium verticillioides*. *J Ind Microbiol Biotechnol.* 2001, 27 (4):241-245; Gargouri M, et al. Fungus beta-glycosidases: immobilization and use in alkyl-beta-glycoside synthesis. *J Mol Catal B: Enzym.* 2004, 29, Issues 1-6:89-94; Lama L, et al. Purification and characterization of thermostable xylanase and β-xylosidase by the thermophilic bacterium *Bacillus thermantarcticus*. *Res Microbiol.* 2004, 155(4):283-289; Belfaquih N & Penninckx M J. A bifunctional β-xylosidase-xylose isomerase from *Streptomyces* sp. EC 10. *Enzyme Microb Technol.* 2000, 27(1-2): 114-121), and some β-xylosidase genes (such as those from several fungus sources) have been cloned and identified successfully (Margolles-Clark E, et al. Cloning of genes encoding alpha-L-arabinofuranosidase and beta-xylosidase from *Trichoderma reesei* by expression in *Saccharomyces cerevisiae*. *Appl Environ Microbiol.* 1996, 62(10):3840-3846.; van Peij N N, et al. β-Xylosidase activity, encoded by xlnD, is essential for complete hydrolysis of xylan by *Aspergillus niger* but not for induction of the xylanolytic enzyme spectrum. *Eur J Biochem.* 1997, 245 (1):164-173; Perez-Gonzalez J A, et al. Molecular cloning and transcriptional regulation of the *Aspergillus nidulans* xlnD gene encoding a β-xylosidase. *Appl Environ Microbiol.* 1998, 64(4):1412-1419; Kitamoto N, et al. Sequence analysis, overexpression, and antisense inhibition of a β-xylosidase gene, xylA, from *Aspergillus oryzae* KBN616. *Appl Environ Microbiol.* 1999, 65(1):20-24; Berrin J G, et al. High-level production of recombinant fungal endo-β-1,4-xylanase in the methylotrophic yeast *Pichia pastoris*. *Protein Expr Purif.* 2000, 19(1): 179-187; Reen F J, et al. Molecular characterisation and expression analysis of the first hemicellulase gene (bxl1) encoding β-xylosidase from the thermophilic fungus *Talaromyces emersonii*. *Biochem Biophys Res Commun.* 2003, 305(3):579-585; Kurakake M, et al. Characteristics of transxylosylation by beta-xylosidase from *Aspergillus awamori* K4. *Biochim Biophys Acta.* 2005, 1726(3):272-279; Wakiyama M, et al. Purification and properties of an extracellular β-Xylosidase from *Aspergillus japonicus* and sequence analysis of the encoding gene. *J Biosci Bioeng.* 2008, 106(4):398-404). However, none of these (natural or recombinant) β-xylosidases was found to have the ability of specifically hydrolyzing 7-xylosyltaxanes. Therefore it is reasonably believed that the genes of β-xylosidases with specific catalytic activity against 7-xylosyltaxane compounds have not been cloned so far, not to mention functional analysis. In fact, a lot of commercial xylosidases, xylanases and other glycosidase did not reveal the ability to remove the xylosyl group from 7-xylosyltaxanes at all (Hanson R L, et al. Enzymatic hydrolysis of 7-xylosyltaxanes by xylosidase from *Moraxella* sp. *Biotechnol Appl Biochem* 1997, 26: 153-158).

SUMMARY OF THE INVENTION

In view of the above-mentioned problems present in the prior arts, the object of this invention is to provide a novel and efficient hydrolase that can specifically hydrolyze the xylosyl group from 7-xylosyltaxanes as well as its gene sequences.

To solve the above-mentioned technical problem, the inventors of the invention made a lot of investigation. Firstly, the specific glycosyl hydrolase (GH) of 7-xylosyltaxanes was purified from the fungi M95.33, which showed specific β-xylosidase activity and could convert 7-xylosyltaxanes to 7-hydroxyltaxanes. The purified enzyme was subjected to LC-MS/MS De novo sequencing and amino acid sequences of some oligopeptides were obtained. Based on amino acid sequences of these oligopeptides, a series of degenerate primers were designed. The cDNA and the structural genes of said enzyme were cloned by molecular biological techniques including nested PCR, RACE, and Genome Walking. The cDNA fragment of the open reading frame (ORF) encoding such enzyme was connected to a suitable expression vector to construct a recombinant plasmid, which was introduced into a corresponding host cell, such as *Pichia pastoris*, which grew fast and could be used for high density fermentation. The recombinant strain could catalyze the glycosyl hydrolysis reaction of 7-xylosyltaxanes in high efficiency to produce 7-hydroxyltaxanes. The inventors have also discovered that this enzyme is a bifunctional enzyme, which can remove the glucose residue from the glucoside by hydrolysis.

This nucleotide sequence exhibits nearly no homology with any other nucleotide sequences that have been registered in GenBank, and the closest sequences are mostly the hypothetical protein gene sequences with the coverage rate of only 3~7% therebetween. The amino acid sequence deduced from the nucleotide sequence is closest to the hypothetical protein sequence (GenBank accession: XP_760179) of *Ustilago maydis*, presenting 43% identity and 59% similarity in a comparable range.

The present invention includes the following contents:

A novel glycosyl hydrolase of 7-xylosyltaxanes, denoted herein as LXYL-P1, is provided.

The second purpose of the present invention is to provide the nucleotide sequence encoding the enzyme.

The third purpose of the present invention is to provide a recombinant plasmid containing the nucleotide sequence.

The forth purpose of the present invention is to provide a host cell containing such a recombinant plasmid or the nucleotide sequence.

The fifth purpose of the present invention is to provide the use of such an enzyme.

To realize the purposes of the present invention, the following technical solutions are adopted.

The present invention provides a glycosyl hydrolase (a bifunctional β-xylosidase-β-glucosidase) of 7-xylosyltaxanes, denoted herein as LXYL-P1.

The amino acid sequence of the glycosyl hydrolase (LXYL-P1) of 7-xylosyltaxanes comprises, an amino acid sequence exhibiting at least 30% identity with the sequence as shown in SEQ ID NO: 2;

preferably an amino acid sequence exhibiting at least 40% identity with SEQ ID NO: 2;
more preferably an amino acid sequence exhibiting at least 50% identity with SEQ ID NO: 2;
further preferably an amino acid sequence exhibiting at least 60% identity with SEQ ID NO: 2;
further preferably an amino acid sequence exhibiting at least 70% identity with SEQ ID NO: 2;
further preferably an amino acid sequence exhibiting at least 80% identity with SEQ ID NO: 2;
further preferably an amino acid sequence exhibiting at least 90% identity with SEQ ID NO: 2;
further preferably an amino acid sequence exhibiting at least 95% identity with SEQ ID NO: 2.

Or, the enzyme is a protein derived from SEQ ID NO: 2 by substitution, deletion or addition of one or several amino acid residues in the amino acid sequence of SEQ ID NO: 2 and having the same activity as that of the amino acid residue sequence of SEQ ID NO: 2.

The present invention also provides a nucleotide sequence or a coding gene encoding said glycosyl hydrolase (LXYL-P1) of 7-xylosyltaxanes, denoted as Lxyl-P1. The nucleotide sequence comprises,
a nucleotide sequence exhibiting at least 30% identity with the nucleotide sequence as shown in SEQ ID NO: 1 or SEQ ID NO: 3;
preferably, a nucleotide sequence exhibiting at least 40% identity with SEQ ID NO: 1 or SEQ ID NO: 3;
more preferably, a nucleotide sequence exhibiting at least 50% identity with SEQ ID NO: 1 or SEQ ID NO: 3;
further preferably, a nucleotide sequence exhibiting at least 60% identity with SEQ ID NO: 1 or SEQ ID NO: 3;
further preferably, a nucleotide sequence exhibiting at least 70% identity with SEQ ID NO: 1 or SEQ ID NO: 3;
further preferably, a nucleotide sequence exhibiting at least 80% identity with SEQ ID NO: 1 or SEQ ID NO: 3;
further preferably, a nucleotide sequence exhibiting at least 90% identity with SEQ ID NO: 1 or SEQ ID NO: 3;
further preferably, a nucleotide sequence exhibiting at least 95% identity with SEQ ID NO: 1 or SEQ ID NO: 3.

Or, the present invention provides a gene from filamentous fungi, which hybridizes under stringent conditions to all or part of the DNA as shown in SEQ ID NO: 1 or SEQ ID NO: 3, or to all or part of a DNA complementary to the sequence as shown in SEQ ID NO: 1 or SEQ ID NO: 3, and which encodes a protein having the activity of hydrolyzing the xylosyl group from 7-xylosyltaxanes.

The present invention also provides a recombinant plasmid containing the nucleotide sequence and encoding LXYL-P1. Said plasmid can be introduced into proper host cells.

The present invention further provides proper host cells that may carry the Lxyl-p1 gene sequence, which comprises a nucleotide sequence exhibiting at least 30% identity with that shown in SEQ ID NO: 1 or SEQ ID NO: 3. The host organisms thereof may be homologous producing hosts of the peptide (LXYL-P1) comprising an amino acid sequence that exhibits at least 30% identity with that shown in SEQ ID NO: 2, or, they may be heterologous host cells.

Suitable host organisms are selected from bacteria, actinomycetes, yeasts, filamentous fungi, plant cells, or animal cells.

Preferred bacteria are selected from *Escherichia* species, *Bacillus* species;
preferred actinomycetes are selected from *Streptomyces* species;
preferred yeasts are selected from *Saccharomyces* species, *Pichia* species and *Schizosaccharomyces* species;
preferred filamentous fungi are selected from *Aspergillus* species, *Trichoderma* species, *Penicillium* species, *Tricholoma* species, *Lentinula* species, and *Agaricus* species;
preferred plant cells are selected from dicotyledon;
preferred animal cells are selected from insect cells.
A preferred *Escherichia* species is preferably *E. coli*;
A preferred *Bacillus* species is preferably *B. subtilis*;
A preferred *Streptomyces* species is preferably *S. lividans*;
A preferred *Saccharomyces* species is preferably *Saccharomyces cerevisiae*;
A preferred *Pichia* species is preferably *P. pastoris*;
A preferred *Schizosaccharomyces* species is preferably *Schizosaccharomyces pombe*;
Preferred *Aspergillus* species are preferably *A. niger*, *A. oryzae*, and *A. nidulans*;
Preferred *Trichoderma* species are preferably *T. reesei* and *T. viride*;
A preferred *Penicillium* species is preferably *Penicillium chrysogenum*;
A preferred *Tricholoma* species is preferably *Tricholoma mongolicum*;
A preferred *Lentinula* species is preferably *L. edodes*;
A preferred *Agaricus* species is preferably *Agaricus bisporus*;
A preferred dicotyledon is preferably *Arabidopsis thaliana*;
Preferred insect cells are preferably *Spodoptera frugiperda* Sf9 cells.

The present invention also provides the nucleotide sequence of this invention, the glycosyl hydrolase of 7-xylosyltaxanes of this invention and the use of host cells comprising the nucleotide sequence of this invention.

In particular, said use is described as follows: suitable host cells were transformed with said DNA by conventional methods in the field, and various substrates, especially the glycoside compounds, are hydrolyzed through the recombinant enzyme produced by the recombinant cells after transformation.

Preferred glycoside compounds to be used as the substrates are selected from compounds comprising the xylosyl residue or compounds comprising the glucosyl residue; that is, the use of the present invention is to remove the xylosyl and/or glucosyl groups from these glycoside compounds by hydrolysis.

Preferred compounds with the xylosyl residue are selected from taxane-xyloside compounds; the substrates are preferably taxane compounds containing the 7-xylosyl residue, that is, 7-xylosyltaxanes, which may be formed naturally, or nonnaturally, for example, by means of chemical synthesis, biosynthesis or semi-synthesis.

As an application of the glycosyl hydrolase of 7-xylosyltaxanes in the present invention, it is preferably used in bioconversion or biocatalysis of 7-xylosyltaxanes to prepare 7-hydroxyltaxanes.

The 7-xylosyltaxanes to be used as the substrates comprise but are not limited to the following compounds: 7-xylosyl-10-deacetyltaxol, 7-xylosyl-10-deacetylcephalomannine, 7-xylosyl-10-deacetyltaxol C, 7-xylosyl-10-deacetyl-baccatin III, 7-xylosyltaxol, 7-xylosylcephalomannine, 7-xylosyl-taxol C, 7-xylosylbaccatin III. The products obtained by hydrolysis after removing the xylosyl group comprise, but are not limited to, the following compounds: 10-deacetyltaxol, 10-deacetylcephalomannine, 10-deacetyltaxol C, 10-deacetyl-baccatin III, paclitaxel, cephalomannine, taxol C, and baccatin III.

These substrates may be used alone or in combination with each other or in a mixture with other taxanes.

The substrates described herein may be selected from a mixture of xylosyl-containing taxane compounds. The mixture includes, but is not limited to, the plant tissues of the *Taxus* genus, which is preferably selected from *T. baccata, T. brevifolia, T. wallichiana, T. media, T. chinensis, T. yunnanensis*, and *T. cuspidate*, or the cell cultures of these plants, or cell cultures of 7-xylosyltaxane-producing microorganisms.

The plant tissues described herein include the roots, needles, bark and whole seedling of the plant.

The structural features of paclitaxel or its analogues (products) prepared by the method provided in this invention and the C-7-xylosyltaxane material (substrate) as used, are shown in formula I:

Formula I

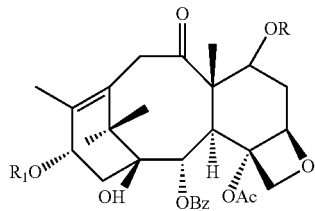

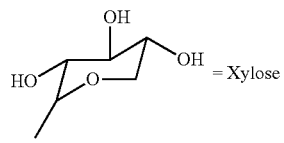 = Xylose

| Compounds | R | $R_1$ | $R_2$ | MW |
|---|---|---|---|---|
| 7-Xylosyl-10-deacetyltaxol, XDT | Xylose | Bz-NH...Ph...OH (C(=O)) | H | 943 |
| 10-Deacetyltaxol, DT | H | | | 811 |
| 7-Xylosyltaxol, XT | Xylose | Bz-NH...Ph...OH (C(=O)) | Ac | 985 |
| Paclitaxel | H | | | 853 |
| 7-Xylosyl-10-deacetylcephalomannine, XDC | Xylose | tigloyl-NH...Ph...OH (C(=O)) | H | 921 |
| 10-Deacetylcephalomannine, DC | H | | | 789 |
| 7-Xylosylcephalomannine, XC | Xylose | tigloyl-NH...Ph...OH (C(=O)) | Ac | 963 |
| Cephalomannine | H | | | 831 |
| 7-Xylosyl-10-deacetylbaccatin III, XDB | Xylose | H | H | 676 |
| 10-Deacetylbaccatin III, DB | H | | | 544 |
| 7-Xylosyl-baccatin III, XB | Xylose | H | Ac | 718 |
| Baccatin III | H | | | 586 |

-continued

Formula I

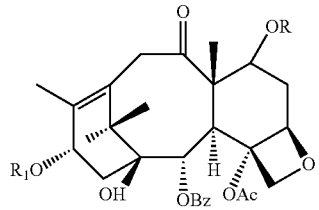

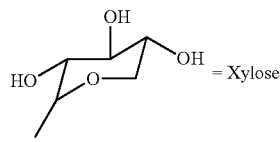 = Xylose

| Compounds | R | $R_1$ | $R_2$ | MW |
|---|---|---|---|---|
| 7-Xylosyl-10-deacetyltaxol C, XDTC | Xylose | (acyl side chain) | H | 937 |
| 10-Deacetyltaxol C, DTC | H | | | 805 |
| 7-Xylosyltaxol C, XTC | Xylose | (acyl side chain) | Ac | 979 |
| Taxol C, TC | H | | | 847 |

Note:
wherein Ph is phenyl; Bz is benzoyl; Ac is acetyl.

The solvents used to dissolve the substrates may be selected from: water, methanol, ethanol, ethyl acetate, acetone, n-hexane, chloroform, dichloromethane, N,N-dimethylformamide (DMF), and dimethyl sulfoxide (DMSO).

The application of the present invention also includes that the glycosyl hydrolase of this invention is used to improve properties of bread dough, improve properties of animal feed, produce D-xylose for manufacture of xylitol, and deink recycled paper. The glycosyl hydrolase of the present invention may further be used in combination with cellulases and hemicellulases to hydrolyze lignocelluloses to obtain monosaccharides for further manufacture of biofuels, such as ethanol and butanol. The glycosyl hydrolase of the present invention may further be used to release bioactive molecules from other glycoside compounds, which may be applied in the pharmaceutical field.

The present invention also provides a bioconversion method for the preparation of paclitaxel and its analogues: 7-xylosyltaxanes are used as the starting materials, and the xylosyl groups of the starting materials are removed by hydrolysis by the host cells containing the gene sequence of the present invention, or by the enzyme produced by the host cells, to obtain paclitaxel or its analogues. The preferred host cells are the fungus or the recombinant strains of the family Tricholomareceae; more preferred host cells are the yeast cells of *Pichia pastoris* of the genus *Pichia*.

In summary, the amino acid sequence of the bifunctional glycosyl hydrolase provided by the present invention comprises an amino acid sequence exhibiting at least 30% identity with the sequence as shown in SEQ ID NO: 2. The bifunctional GH provided by the present invention can be used to remove the xylosyl residue or glucosyl residue from 7-xylosyltaxanes or other glycoside compounds. The present invention also relates to the recombinant plasmids and the host cells, both of which containing the nucleotide sequences as described above. Furthermore, the present invention relates to the application of the glycosyl hydrolase of 7-xylosyltaxanes or the host cells containing the glycosyl hydrolase of 7-xylosyltaxanes in removing the xylosyl group and/or glucosyl group by hydrolysis.

The glycosyl hydrolase of 7-xylosyltaxanes provided by the present invention, which has a definite amino acid sequence and bifunctional properties of β-xylosidase-β-glucosidase, is produced by *Lentinula edodes* M95.33, a fungus of the family Tricholomareceae, or by the recombinant cells containing the coding gene of the enzyme. The enzyme may be present in the cells or secreted outside of the cells and can be used for the conversion of 7-xylosyltaxanes to paclitaxel or its analogues.

The nucleotide sequence encoding the glycosyl hydrolase according to this invention includes a complete open reading frame (ORF), which may be used to construct varied types of recombinant expression plasmids that can be transferred into the original fungus or other fungal hosts, or be transferred into prokaryotic cells (including *E. coli*, actinomycetes), plant cells and animal cells, and the like host cells. These hosts may acquire the ability of hydrolyzing 7-xylosyltaxanes into 7-hydroxyltaxanes due to the expression of the glycosyl hydrolase gene. The recombinant hosts may also be used for biotransformation of other sugar-containing compounds.

The application of the present invention also includes that the glycosyl hydrolase of this invention is used to improve properties of bread dough, improve properties of animal feed, produce D-xylose for manufacture of xylitol, and deink recycled paper. Furthermore, the glycosyl hydrolase provided by the present invention may be used in combination with cellulases and hemicellulases and so on to hydrolyze lignocelluloses to obtain monosaccharides for further manufacture of biofuels, such as ethanol and butanol. Moreover, the glycosyl hydrolase of the present invention may be used to release the bioactive molecules from other glycoside compounds, which may be applied in the pharmaceutical field.

The Beneficial Technical Effects

The present invention has cloned and heterologously expressed, for the first time, the gene encoding a glycosyl hydrolase that may specifically catalyze 7-xylosyltaxanes to 7-hydroxyltaxanes, and has constructed the bio-engineered strains having the activity of such enzyme, and thus provides a novel and effective way for the large-scale production of 7-hydroxyltaxanes.

Terms And Abbreviations

CDS: the coding sequence of a protein, which is from the start codon to the stop codon.

DETAILED DESCRIPTION OF THE INVENTION

Figure 1:
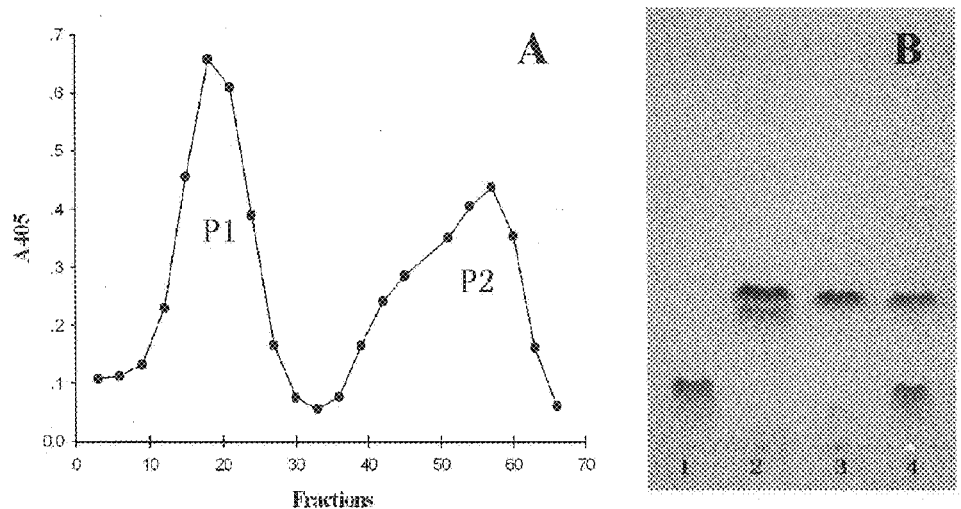
FIG. 1: Phenyl Sepharose hydrophobic column chromatography of the β-xylosidase-β-glucosidase from the protein extract of the fungus M95.33 (A), and thin layer chromatography (TLC) of XDT conversion (B).
A: P1. active elution peak of LXYL-P1; P2. active elution peak of LXYL-P2. The horizontal ordinate shows different fractions (numberings of collecting tubes of different fractions), and the vertical axis is absorption value of A405 (405 nm)
B: 1. XDT (control); 2. DT (control); 3. XDT bioconversion by LXYL-P1; 4. XDT bioconversion by LXYL-P2.

The present invention is further illustrated by the following examples which are illustrative only and which are by no means meant to limit the scope of the present claims.

Example 1

Purification of *L. edodes* β-xylosidase-β-glucosidase (LXYL-P1)

Cultivation of the fungus M95.33. About 1 cm² of lawn picked from a mycelial slant after cultivation was inoculated and grown in 100 ml sterile wheat bran liquid medium [contains per liter: 50.00 g wheat bran (added with appropriate amount of water, boiled for 30 min and then filtrated to quit the solid residue), 20.00 g peptone, 1.50 g $KH_2PO_4$, 0.75 g $MgSO_4$, natural pH~6.3] for 6~8 days at 25~26° C. and 160 rpm in an orbital shaker.

Isolation, Purification and Analysis on the Glycosyl Hydrolase. The mycelium was harvested by filtration. After grinding with liquid nitrogen, 3~5 volumes of 50 mM Tris-HCl cell lysis buffer (pH 8.0) was added and then the resultant was subjected to ultrasonic treatment for 5 min on ice (130 W, 10 seconds each time with a 10-second interval). The supernatant was collected after centrifugation (12000 rpm, 10 min), which was used as the crude enzyme solution for further isolation and purification.

Protein with β-xylosidase activity was monitored by using the p-nitrophenyl-β-D-xylopyranoside (PNP-Xyl) as a specific chromogenic substrate. One unit of enzyme was defined as the amount of enzyme that is necessary to produce 1 nmol of p-nitrophenol by catalysis in 1 min at 50° C. and pH 5.0 with PNP-Xyl as the substrate.

The above crude enzyme solution (80~90 ml each time) was applied to a DEAE Sepharose FF anion exchange column (1.6 cm×20 cm) equilibrated with Tris-HCl buffer (50 mM, pH 8.0). Elution was performed with 50 mM Tris-HCl buffer (pH 8.0) with a gradient of 0, 0.1, 0.25, and 2.0 M NaCl (at a flow rate of 2 ml/min). Fractions of 0.1~0.25 M NaCl eluent having enzyme activity were collected and added with 1 M $(NH_4)_2SO_4$ for the subsequent chromatography.

The fraction eluted in the above step was applied to a Phenyl Sepharose hydrophobic column (1.6 cm×20 cm) equilibrated with 50 mM Tris-HCl buffer (pH 8.0) containing 1 M $(NH_4)_2SO_4$. Elution was performed with Tris-HCl buffer (50 mM, pH8.0) having a linear gradient of 1.0~0 M $(NH_4)_2SO_4$ (at a flow rate of 2 ml/min). Fractions having enzymatic activity were collected and dialyzed with Tris-HCl buffer (50 mM, pH8.0).

The dialyzed solution was applied to a DEAE Sepharose FF anion exchange column (1.6 cm×20 cm, equilibrated with 50 mM Tris-HCl buffer, pH 8.0). Elution was performed with a linear gradient of 0.1~0.25 M NaCl in Tris-HCl buffer (50 mM, pH8.0) at a flow rate of 2 ml/min. Fractions with the highest enzyme activity were collected, concentrated and applied to a Sephacryl S200 HR molecular sieve chromatography column [1.6 cm×60 cm, equilibrated with Tris-HCl buffer (50 mM, pH 8.0) containing 0.1 M NaCl]. Elution was performed with 0.1 M NaCl in Tris-HCl buffer (50 mM, pH 8.0) at a flow rate of 0.5 ml/min. Fractions with the highest enzyme activity were collected. Finally the purified enzyme was obtained.

Procedures for the purification described above are generalized as follows:

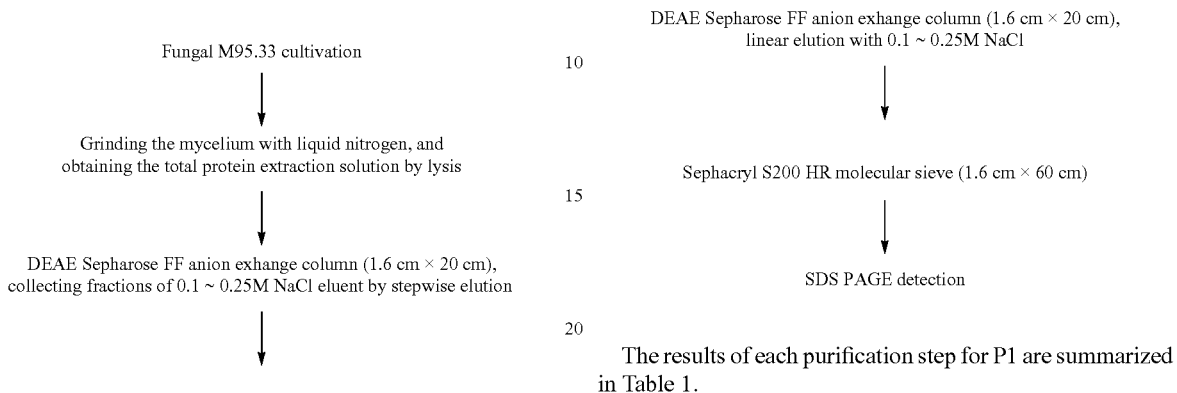

The results of each purification step for P1 are summarized in Table 1.

TABLE 1

| Purification step | Volume (ml) | Total protein (mg) | Total activity (U) | Specific activity (U/mg) | Recovery ratio (%) | Purification fold |
|---|---|---|---|---|---|---|
| Crude enzyme solution | 510 | 527.8 | 4099550.9 | 7767.2 | 100 | 1 |
| DEAE Sepharose FF | 225 | 91.8 | 1384245.0 | 15078.9 | 33.77 | 1.94 |
| Phenyl Sepharose | 120 | 8.27 | 1103753.3 | 133464.7 | 26.92 | 17.18 |
| DEAE Sepharose FF | 25 | 0.625 | 426201.8 | 681922.8 | 10.40 | 87.79 |
| Sephacryl S200 HR | 3 | 0.048 | 161373.8 | 3361954.7 | 3.94 | 432.84 |

Two separate peaks [named LXYL-P1 (or P1) and LXYL-P2 (or P2), respectively] exhibiting β-xylosidase activity were obtained by elution in a linear gradient with the Phenyl Sepharose hydrophobic column. Both P1 and P2 could hydrolyze 7-xylosyl-10-deacetyltaxol (XDT) into 10-deacetyltaxol (DT) (as shown in FIG. 1). In FIG. 1, penal A showed the enzymatic activity peaks obtained by chromatography; penal B showed the thin layer chromatography (TLC) of the substrate XDT conversion by enzymatically active samples P1 and P2, respectively. Within penal B, 1 was XDT control; 2 was DT control; 3 was XDT conversion by P1; and 4 was XDT conversion by P2. LC-MS/MS De novo sequencing results implied that P1 and P2 possessed the same amino acid residue sequence but are different in glycosylation forms.

The reaction formula showing XDT being hydrolyzed into DT and xylose is illustrated as below:

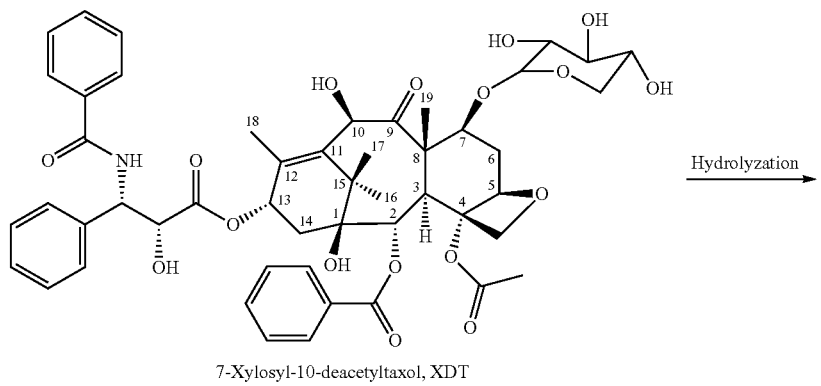

7-Xylosyl-10-deacetyltaxol, XDT

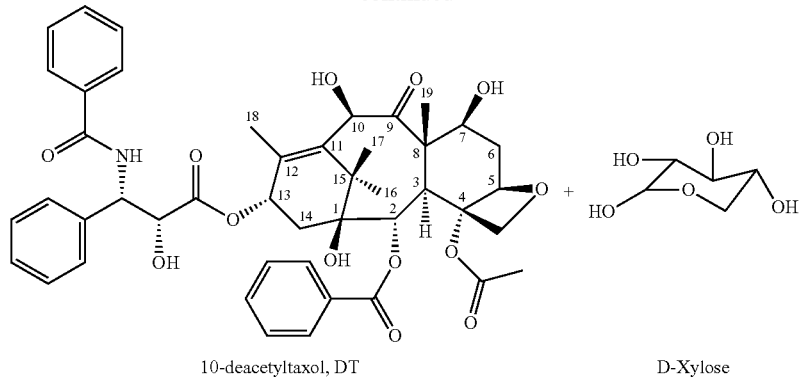

10-deacetyltaxol, DT    D-Xylose

Example 2

Specificity Test on Different Glycoside Substrates Hydrolysis by LXYL-P1 (or P1) Protein In addition to the β-xylosidase activity, especially the activity of hydrolyzing 7-xylosyltaxanes, the specificity of the LXYL-P1 (or P1) on other glycoside substrates was also tested by employing four chromogenic substrates: p-nitrophenyl-β-D-glucopyranoside (PNP-Glc), p-nitrophenyl-β-D-galactopyranoside (PNP-Gal), p-nitrophenyl-α-L-arabinopyrano side (PNP-Ara), and p-Nitrophenyl-β-D-xylopyranoside (PNP-Xyl, serving as a control). Each of the chromogenic substrates was prepared in 50 mM acetate buffer to obtain 5 mM solution (pH 5.0).

To the purified P1 protein diluent (25 µl) obtained in example 1, 100 µl of each chromogenic substrate was added. The reaction was performed at 50° C. for 20 min and stopped with 2 ml saturated solution of sodium borate. Release of p-nitrophenol (absorbance value) was measured at 405 nm. The result showed that, P1 protein could hydrolyze PNP-Glc and PNP-Xyl, but not PNP-Gal and PNP-Ara. The results are shown in Table 2.

TABLE 2

| Substrates | $OD_{405}$ value | Relative activity (% control) |
|---|---|---|
| p-nitrophenyl-β-D-xylopyranoside (PNP-Xyl) | 0.745 | 100 |
| p-nitrophenyl-β-D-glucopyranoside (PNP-Glc) | 1.615 | 217 |
| p-nitrophenyl-β-D-galactopyranoside (PNP-Gal) | 0.000 | 0 |
| p-nitrophenyl-α-L-arabinopyranoside (PNP-Ara) | 0.000 | 0 |

Example 3

Cloning of the Encoding Gene (Lxyl-p1) of the Glycosyl Hydrolase LXYL-P1

Figure 2:
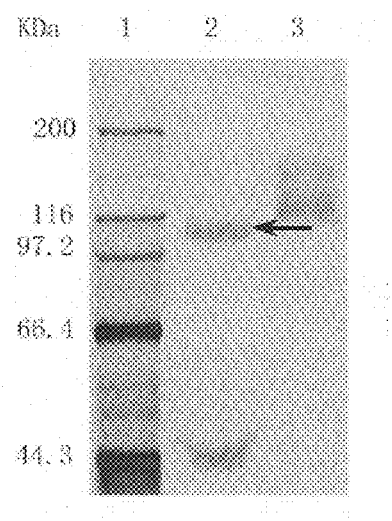
FIG. 2: Electrophoresis (SDS-PAGE) of the LXYL-P1.
1. molecular weight marker of protein; 2. LXYL-P1 treated by reduction; 3. LXYL-P1 treated by non-reduction. The protein band for LC-MS/MS analysis is shown by the arrow.

LXYL-P1 obtained in Example 1 was subjected to SDS-PAGE electrophoresis (see FIG. 2), and the electrophoretic band with an apparent molecular weight of about 110 kDa after reduction treatment was recovered and subjected to LC-MS/MS analysis. The five oligopeptides with the highest peaks were selected and subjected to De novo sequencing and the amino acid residue sequences of the five oligopeptides were obtained as follows:

```
1.   LPWTWGK                    (SEQ ID NO: 4)
2.   QSGSLPLQHPQR               (SEQ ID NO: 5)
3.   HWLAYEQETSR                (SEQ ID NO: 6)
4.   DLPVGDSAVVTYPPR            (SEQ ID NO: 15)
5.   TLTPLEALQK                 (SEQ ID NO: 16)
     (Wherein I and L,
     K and Q are not
     distinguishable)
```

Bioinformatic approaches were applied to assess the relative locations of the five oligopeptides, and the order thereof on LXYL-P1 was determined to be: 3, 2, 5, 1, 4. Forward and reverse degenerate primers were designed as follows respectively according to oligopeptides 3 and 5:

```
3F1:   CTTGCGTACGAGCARGARAC       (SEQ ID NO: 7)
3F2:   CACTGGCTTGCGTAYGARCA       (SEQ ID NO: 8)
3F3:   CACTGGCTTGCNTAYG           (SEQ ID NO: 9)
5R1:   AGCCTCCAGTGGCGTNAGNGT      (SEQ ID NO: 10)
5R2:   CTGCAGAGCCTCCAGNGGNGT      (SEQ ID NO: 11)
5R3:   TTCTGCAGAGCCTCNAGNGG       (SEQ ID NO: 14)
```

Figure 8:
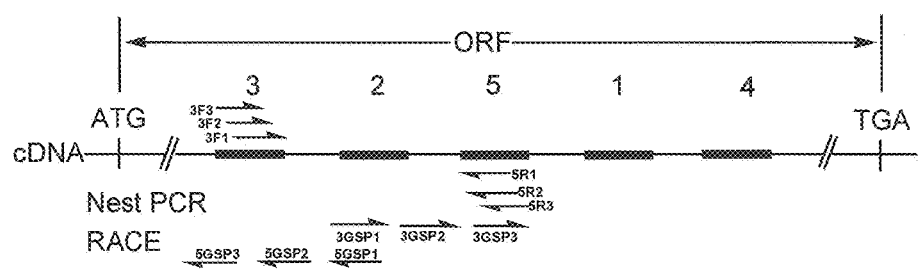
FIG. 8: Schematic diagram of the PCR amplification process.

The total RNA from the fungus M95.33 was used as the template and nest-PCR was performed by using the degenerate primers as described above. It was confirmed that the PCR products contained the coding sequences of the oligopeptides 3, 2 and 5. Then RACE technique was applied in elongation at both ends to obtain the cDNA fragment containing the coding region of the above-mentioned five oligopeptides. This fragment contains an open reading frame (ORF, or referred to as CDS, named Lxyl-p1) of 2412 by which encodes 803 amino acids. The cDNA sequence (SEQ ID NO: 3) and the amino acid sequence (SEQ ID NO: 2) encoded by this cDNA sequence are shown in the sequence list. The PCR amplification process is shown in FIG. 8.

Specific primers were designed according to this cDNA sequence, and the structural gene sequence (G-Lxyl-p1) of LXYL-P1 was obtained by PCR amplification and Genome Walking technique, using the genomic DNA from the fungus M95.33 as the template. At the genomic level, the gene herein consists of 19 exons and 18 introns, with a length of 3608 by from the start codon ATG to the stop codon TGA. The nucleotide sequence (SEQ ID NO: 1) is shown in the sequence list.

Example 4

Figure 3:
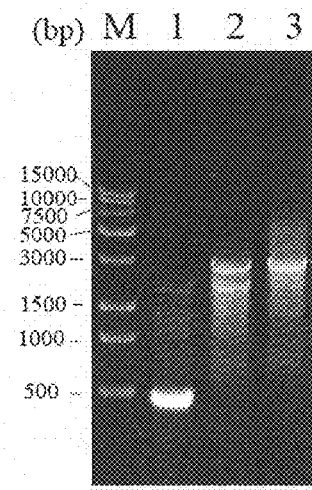
FIG. 3: Agarose gel electrophoresis of colony PCR identification on the recombinant yeasts.
M. molecular marker; 1. the recombinant strain GS115-9K (control, transformed with pPIC9K); 2. the recombinant strain GS115-9K-P1-2 (transformed with pPIC9K-P1-2); 3. the recombinant plasmid pPIC9K-P1-2 (control).

Construction of the Recombinant Plasmids and Screening of the Recombinant Yeasts SnaB I and Not I restriction enzyme sites were introduced by PCR to the 5'- and 3'-ends of the ORF (Lxyl-p1) of P1 coding region obtained in Example 3, respectively. After digestion with SnaB I/Not I, the resultant was then ligated to the *Pichia pastoris* expression vector pPIC9K (secreted expression vector) or pPIC3.5K (non-secretory expression vector), which was also digested with SnaB I/Not I, obtaining the recombinant expression plasmid pPIC9K-P1-2 or pPIC3.5K-P1-2. The recombinant plasmid was linearized by Sac I restriction enzyme and then transformed into the GS115 competent cells of *Pichia pastoris* by the electroporation transformation method. Meanwhile, the null vector pPIC9K or pPIC3.5K was also introduced into the GS115 competent cells of *Pichia pastoris* by the same method, respectively, as the control. The transformed yeast cells were spread on the MD plate [contains per liter: 20.00 g glucose, 13.40 g YNB (yeast nitrogen base without amino acids), 0.4 mg biotin, 15.00 g agar] and incubated at 28° C. for 2~3 d. Single colony was picked up and inoculated on the YPD-Geneticin® resistant plate (contains per liter: 10.00 g yeast extract, 20.00 g peptone, 20.00 g glucose, 15.00 g agar, ≤4.00 g G418), and the cultivation was continued for another 2~3 days to screen resistant colonies. The resistant colonies were subjected to colony PCR identification. Here are the examples of the transformants of pPIC9K and pPIC9K-P1-2 (FIG. 3).

PCR primers match with the AOXI sequences at the two sides of the cloning site in the pPIC9K vector, respectively:

```
                                    (SEQ ID NO: 13)
5' GACTGGTTCCAATTGACAAGC 3'

(SEQ ID NO: 12)
Reverse: 5' GGCAAATGGCATTCTGACATCC 3'
```

The strain transformed with the null vector pPIC9K gave an amplified fragment of 492 bp; while both the recombinant plasmid pPIC9K-P1-2 and its transformed strain gave an amplified fragment of 2910 bp. In FIG. 3, 1 showed the amplification result of the control recombinant yeast genome introduced with the null vector pPIC9K; 2 showed the amplification result of the recombinant yeast genome introduced with pPIC9K-P1-2; and 3 showed the amplification result of the control recombinant plasmid pPIC9K-P1-2.

Figure 4:
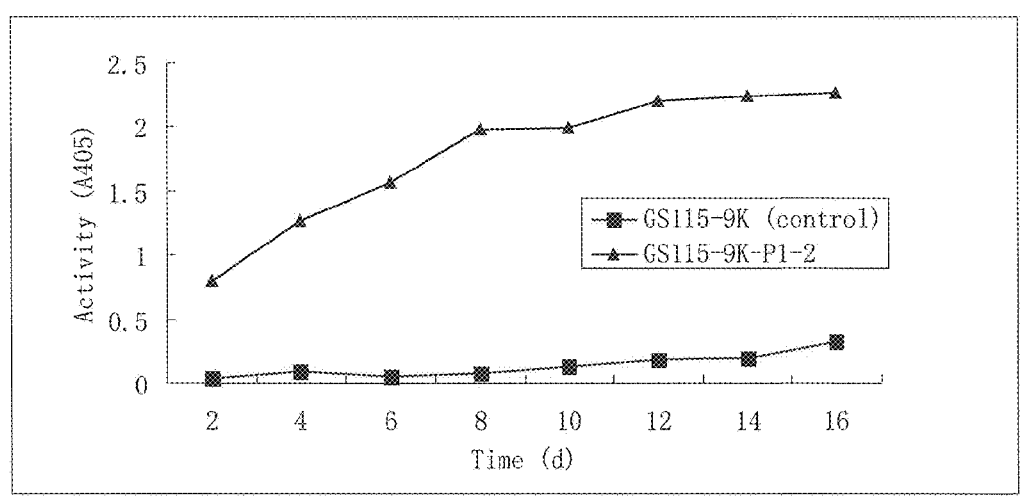
FIG. 4: Comparison of the recombinant strains GS115-9K-P1-2 and GS115-9K (control) on β-xylosidase activity.

BMGY medium (contains per liter: 10.00 g yeast extract, 20.00 g peptone, 100 mM potassium phosphate buffer, pH 6.0, 10 ml glycerol) and BMMY medium (10 ml glycerol in BMGY medium was replaced with 10 ml methanol as the carbon source) were used as the seed culture and fermentation media respectively for the recombinant yeast. The resistant strain obtained by screening was inoculated into 10 ml seed culture medium and incubated at 30° C., 220 rpm for 18 h. The cultures were washed 2 times by centrifugation and the cell pellet was transferred into 50 ml fermentation medium. Cells were cultured at 30° C., 220 rpm, and 1% methanol was added every 24 h for induction of expression of the recombinant protein. Meanwhile the enzyme activity of the recombinant strain was detected regularly. The samples were washed 2 times with distilled water by centrifugation and the cell pellet was suspended in the same volume of distilled water. To 50 μl of the cell suspension, 100 μl of 5 mM PNP-Xyl was added and allowed to react for 20 min at 30~55° C. It could be seen that the recombinant strain has the ability to hydrolyze the substrate PNP-Xyl while the control strain that was transformed with null vector did not show such ability (see FIG. 4). In addition, no obvious enzymatic activity was detected in the supernatant of the fermentation broth of the recombinant strain, implying that the recombinant enzyme was mainly in the cells.

Example 5

Hydrolysis of 7-xylosyl-10-deacetyltaxol (XDT) by the Recombinant Yeast

The recombinant yeast GS115-9K-P1-2 (transformant of the recombinant expression plasmid pPIC-9K-P1-2) obtained in example 4 was cultured and induced for 5 days in the manner of Example 4. Cells were centrifuged, harvested and washed, and then was, directly or after lyophilization, suspended with 50 mM acetate buffer or phosphate buffer (65 mg wet cells/ml or 16 mg dry cells/ml, pH 3.5~7.5), and used as the hydrolytic reaction solution. To 20 ml of the cell reaction solution, 0.5 ml solution of 7-xylosyl-10-deacetyltaxol (XDT) was added with the final concentration of XDT being 0.625 mg/ml. The resultant was incubated in a water shaking bath for 12 h at 30~55° C.

Extraction was performed with ethyl acetate after the reaction was completed. TLC analysis showed that the substrate was completely transformed. HPLC [conditions: column: Agilent Eclipse XDB-C18 (4.6×150 mm, 5 μm), mobile phase: acetonitrile (38%~52%), flow rate: 1 ml/min, column temperature: 28° C., detection wavelength: 230 nm] was used to analyze the contents of the XDT substrates and DT products in the extract, showing a conversion ratio of 98.80%.

Figure 5:
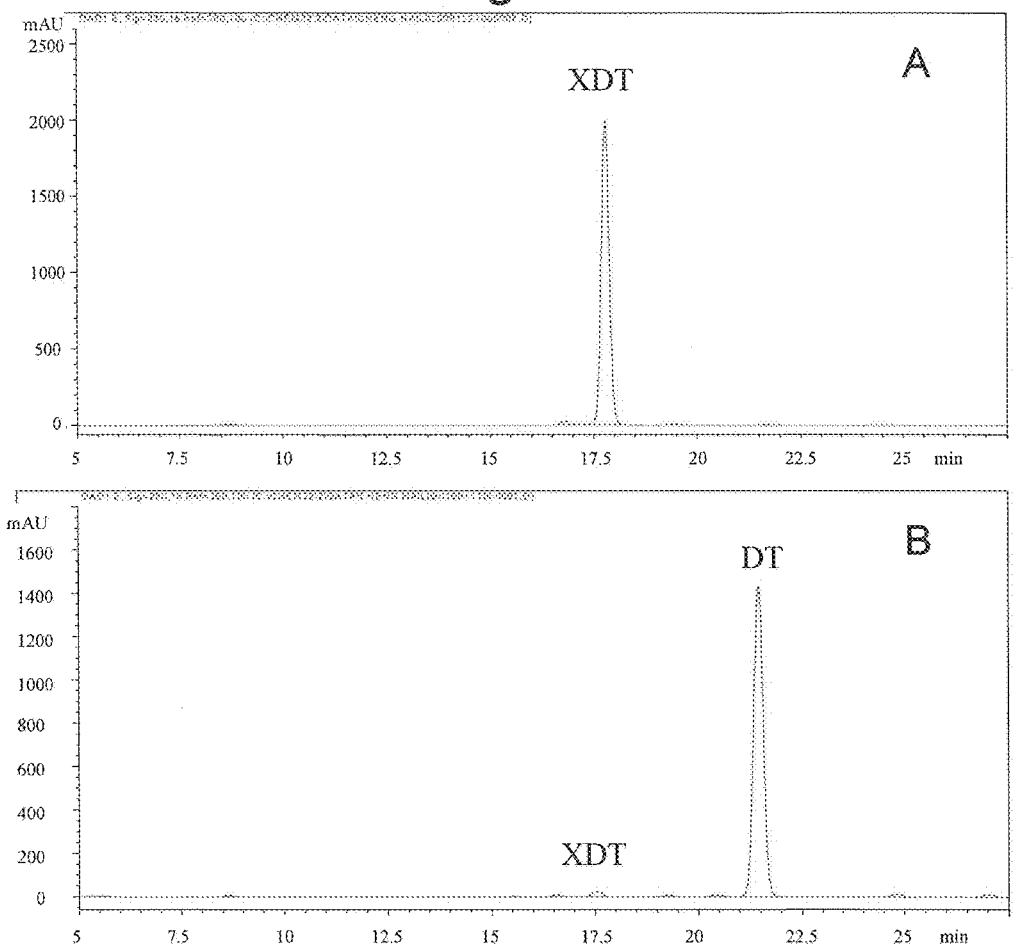
FIG. 5: HPLC analysis of XDT conversion by the recombinant strain GS115-9K-P1-2.
A. before conversion; B. after conversion.

HPLC analysis on the XDT hydrolytic reaction result by the recombinant yeast is shown in FIG. 5, wherein A is before conversion, while B is after conversion.

Example 6

Hydrolysis of 7-xylosyltaxane Mixtures by the Recombinant Yeast

The recombinant yeast GS115-3.5K-P1-2 (transformant of the recombinant expression plasmid pPIC3.5K-P1-2) obtained in Example 4 was applied in the following bioconversion reaction, wherein the substrates to be converted were 7-xylosyltaxane mixtures, the main components of which included 62.12% of 7-xylosyl-10-deacetyltaxol, 12.75% of 7-xylosyl-10-deacetylcephalomannine, 17.04% of 7-xylosyl-10-deacetyltaxol C, and 8.09% of other components.

The method for culturing the recombinant strain was the same as in Example 5. 16 ml 7-xylosyltaxane mixtures (at a concentration of 100 mg/ml) were added to 200 ml recombinant strain reaction solution with the final concentration of the 7-xylosyltaxane mixtures being about 8 mg/ml (supersaturated). The recombinant yeast introduced with the null vector was taken as the negative control. The solution was mixed by magnetic stirring for 24 h at 30~55° C. HPLC analysis was used to analyze the contents of substrates and products in the conversion system as the method in Example 5 after the reaction was completed (FIG. 6), showing the following conversion ratios: 7-xylosyl-10-deacetyltaxol (XDT), 92.45%; 7-xylosyl-10-deacetylcephalomannine (XDC), 93.60%; and 7-xylosyl-10-deacetyltaxol C (XDTC), 92.00%. The yields of the three main products: 10-deacetyl-taxol (DT): 3.27 mg/ml; 10-deacetylcephalomannine (DC): 0.74 mg/ml; and 10-deacetyltaxol C (DTC): 0.92 mg/ml. The total yield of the three main products was 4.93 mg/ml; while the control did not show any of the above activities (FIG. 6).

Figure 6:
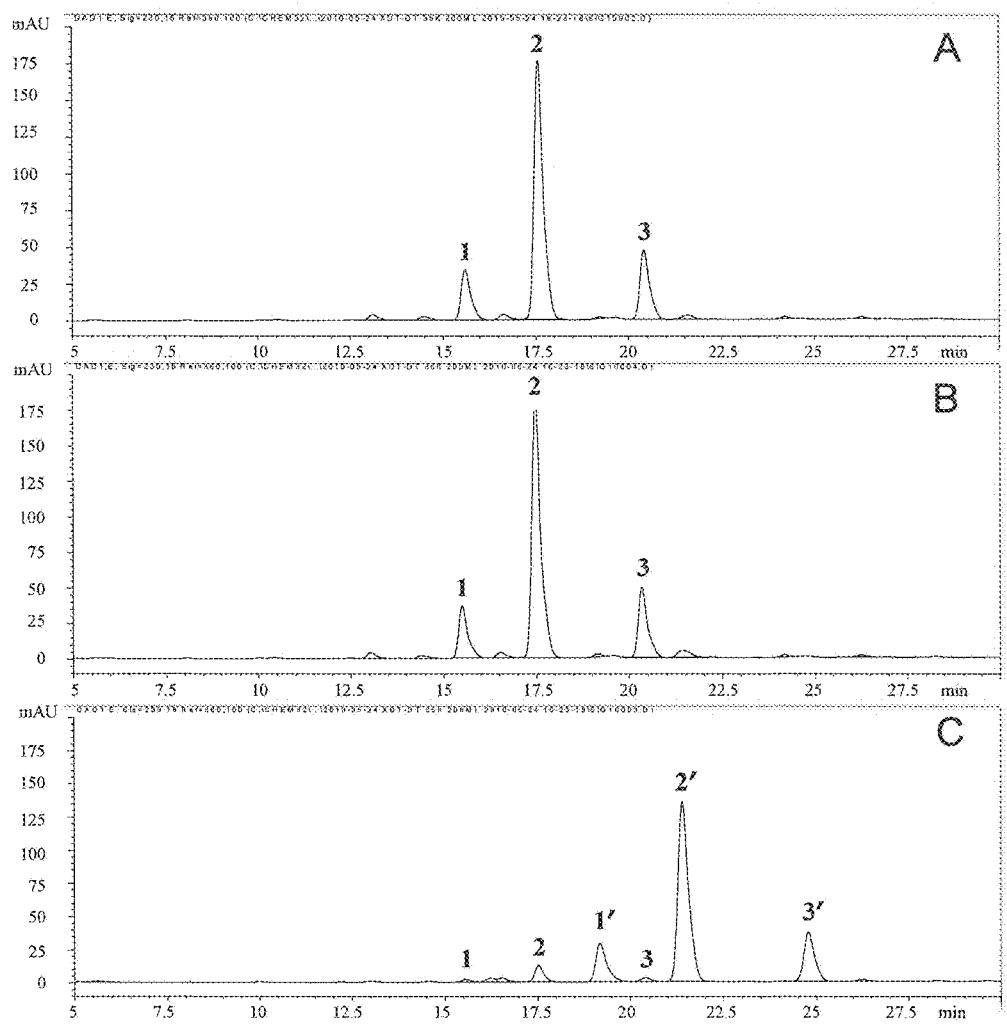
FIG. 6: HPLC analysis of conversion of 7-xylosyltaxane mixtures by the recombinant strain GS115-3.5K-P1-2.
A. the mixed substrates (control); B. recombinant yeast GS115-3.5K introduced with a null vector (pPIC3.5K)+ the mixed substrate (control); C. recombinant yeast GS115-3.5K-P1-2 introduced with the plasmid pPIC3.5K-P1-2 harboring Lxyl-p1 gene+the mixed substrate. 1, 2 and 3 represent 7-xylosyl-10-deacetylcephalomannine (XDC), 7-xylosyl-10-deacetyltaxol (XDT), and 7-xylosyl-10-deacetyltaxol C (XDTC), respectively; and 1', 2' and 3' represent the corresponding products of xylosyltaxane, i.e., 10-deacetylcephalomannine (DC), 10-deacetyltaxol (DT), and 10-deacetyltaxol C (DTC), respectively.

In FIG. 6, A showed the mixed substrates (control); B showed the recombinant yeast introduced with the null vector+mixed substrates (control); C showed the recombinant strain introduced with Lxyl-p1 gene+mixed substrates. 1 was 7-xylosyl-10-deacetylcephalomannine; 2 was 7-xylosyl-10-deacetyltaxol; 3 was 7-xylosyl-10-deacetyltaxol C; and 1', 2' and 3' were the corresponding products of 7-xylosyltaxanes, respectively.

Example 7

Hydrolysis of 7-xylosyl-baccatin III (XDB) by the Recombinant Yeast

Figure 7:
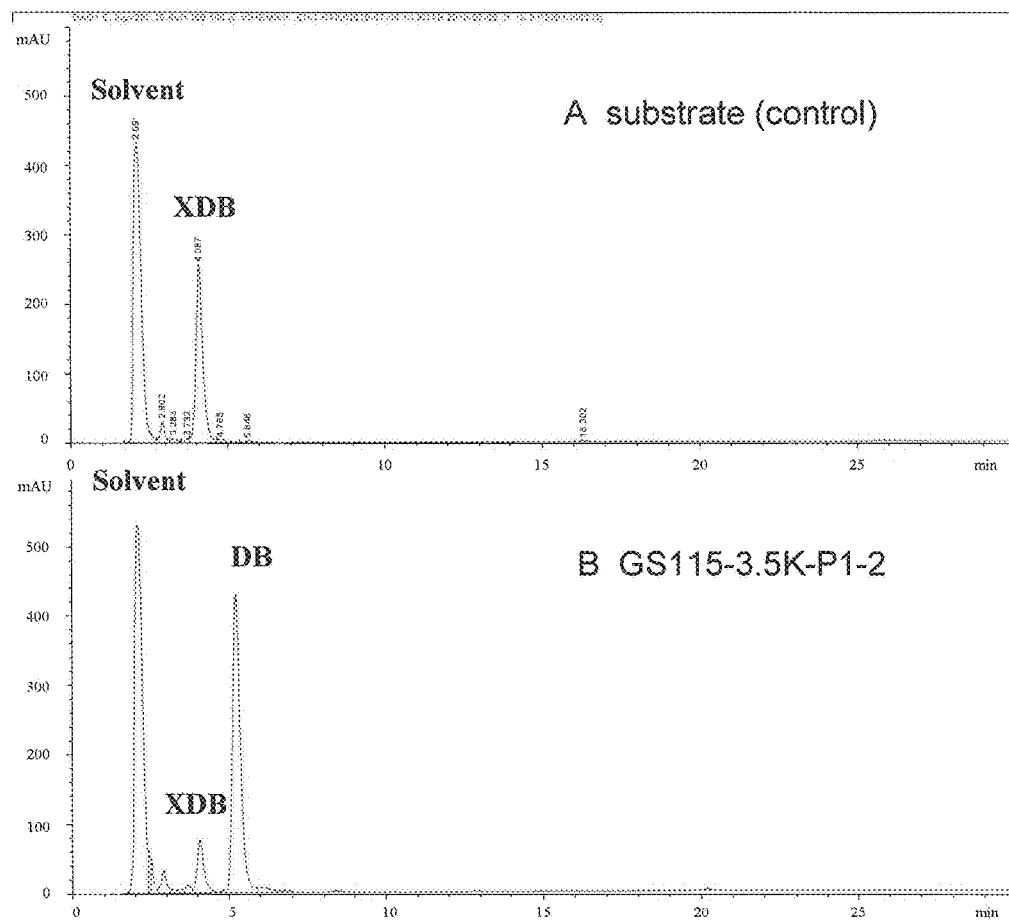
FIG. 7: HPLC analysis of conversion of 7-xylosyl-10-deacetylbaccatin III by the recombinant strain GS115-3.5K-P1-2 (the solvent peak with a retention time of 2 min is prior to XDT).

The strain was the same as that in Example 6 and the substrate was 7-xylosyl-10-deacetylbaccatin III (XDB). 1.5 ml cell reaction solution contained 16 mg dry cells per milliliter and 8 mg XDB per milliliter. The mixture was incubated in a water shaking bath for 24 h at 30~55° C. HPLC analysis results showed that the conversion ratio of XDB was 86.54% and the yield of the product, 10-deacetylbaccatin III (DB), was 5.57 mg/ml (FIG. 7).

The invention claimed is:

1. A glycosyl hydrolase comprising an amino acid sequence that has at least 95% amino acid sequence identity with the amino acid sequence of SEQ ID NO: 2, wherein said glycosyl hydrolase has glycosyl hydrolase activity and is recombinantly produced by expressing said glycosyl hydrolase in a *Pichia pastoris* host cell.

2. The glycosyl hydrolase of claim 1, wherein the glycosyl hydrolase has β-xylosidase activity.

3. A *Pichia pastoris* host cell comprising a recombinant expression plasmid, wherein the recombinant expression plasmid comprises a polynucleotide encoding the glycosyl hydrolase of claim 1.

4. A method for hydrolyzing a glycoside compound comprising a xylosyl group and/or a glucosyl group, the method comprising
contacting the glycosyl hydrolase of claim 1 with the glycoside compound to remove the xylosyl group and/or to remove the glucosyl group of the glycoside compound by hydrolysis.

5. A method for hydrolyzing glycoside compounds comprising a xylosyl group and/or a glucosyl group, the method comprising
contacting the host cell of claim 3 with the glycoside compounds to remove the xylosyl group and/or to remove the glucosyl group of the glycoside compounds by hydrolysis.

6. The method of claim 5, wherein the glycoside compounds comprising a xylosyl group are selected from taxane-xyloside compounds.

7. The method of claim 6, wherein the taxane-xyloside compounds are selected from 7-xylosyltaxane compounds.

8. The method of claim 7, wherein the 7-xylosyltaxane compounds are selected from
7-xylosyltaxol,
7-xylosyl-10-deacetyltaxol,
7-xylosylcephalomannine,
7-xylosyl-10-deacetylcephalomannine,
7-xylosyltaxol C,
7-xylosyl-10-deacetyltaxol C,
7-xylosylbaccatin III, and
7-xylosyl-10-deacetylbaccatin III.

9. The method of claim 8, wherein the products obtained after removing the xylosyl group by hydrolysis with the glycosyl hydrolase are 7-hydroxyltaxane compounds selected from
paclitaxel,
10-deacetyltaxol,
cephalomannine,
10-deacetylcephalomannine,
taxol C,
10-deacetyltaxol C,
baccatin III, and
10-deacetylbaccatin III.

10. The method of claim 7, wherein the 7-xylosyltaxane compounds are selected from mixtures of 7-xylosyltaxane compounds.

11. The method of claim 10, wherein the mixtures of 7-xylosyltaxane compounds are from plant tissues of the *Taxus* genus, cell cultures of plants of the *Taxus* genus, or cell cultures of microorganisms capable of generating 7-xylosyltaxane compounds.

12. The method of claim 11, wherein the plants of the *Taxus* genus are selected from *T. baccata, T. brevifolia, T. wallichiana, T. media, T. chinensis, T. yunnanensis*, and *T. cuspidate*.

13. The method of claim 11, wherein the plant tissues of the *Taxus* genus are selected from roots, needles, bark or whole seedlings.

14. The method of claim 7 wherein a solvent is used in the hydrolysis of the 7-xylosyltaxanes, wherein the solvent is water, methanol, ethanol, ethyl acetate, acetone, n-hexane, chloroform, dichloromethane, N,N-dimethylformamide (DMF), or dimethyl sulfoxide (DMSO).

15. A method for hydrolyzing lignocelluloses to obtain monosaccharides, the method comprising contacting the lignocelluloses with the glycosyl hydrolase of claim 1 together with cellulases and/or hemicellulases to hydrolyze lignocelluloses to obtain monosaccharides.

* * * * *

SEQUENCE LISTING

```
<160> NUMBER OF SEQ ID NOS: 16

<210> SEQ ID NO 1
<211> LENGTH: 3608
<212> TYPE: DNA
<213> ORGANISM: Lentinula edodes
<220> FEATURE:
<221> NAME/KEY: misc_feature
<222> LOCATION: (1)..(154)
<223> OTHER INFORMATION: exon
<220> FEATURE:
<221> NAME/KEY: misc_feature
<222> LOCATION: (155)..(218)
<223> OTHER INFORMATION: intron
<220> FEATURE:
<221> NAME/KEY: misc_feature
<222> LOCATION: (219)..(307)
<223> OTHER INFORMATION: exon
<220> FEATURE:
<221> NAME/KEY: misc_feature
<222> LOCATION: (308)..(360)
<223> OTHER INFORMATION: intron
<220> FEATURE:
<221> NAME/KEY: misc_feature
<222> LOCATION: (361)..(588)
<223> OTHER INFORMATION: exon
<220> FEATURE:
<221> NAME/KEY: misc_feature
<222> LOCATION: (589)..(645)
<223> OTHER INFORMATION: intron
<220> FEATURE:
<221> NAME/KEY: misc_feature
<222> LOCATION: (646)..(667)
<220> FEATURE:
<221> NAME/KEY: misc_feature
<222> LOCATION: (668)..(719)
<220> FEATURE:
<221> NAME/KEY: misc_feature
<222> LOCATION: (720)..(738)
<220> FEATURE:
<221> NAME/KEY: misc_feature
<222> LOCATION: (739)..(794)
<220> FEATURE:
<221> NAME/KEY: misc_feature
<222> LOCATION: (795)..(906)
<223> OTHER INFORMATION: exon
<220> FEATURE:
<221> NAME/KEY: misc_feature
<222> LOCATION: (907)..(962)
<223> OTHER INFORMATION: Intron
<220> FEATURE:
<221> NAME/KEY: misc_feature
<222> LOCATION: (963)..(1017)
<223> OTHER INFORMATION: exon
<220> FEATURE:
<221> NAME/KEY: misc_feature
<222> LOCATION: (1018)..(1078)
<220> FEATURE:
<221> NAME/KEY: misc_feature
<222> LOCATION: (1079)..(1103)
<223> OTHER INFORMATION: exon
```

```
<220> FEATURE:
<221> NAME/KEY: misc_feature
<222> LOCATION: (1104)..(1163)
<220> FEATURE:
<221> NAME/KEY: misc_feature
<222> LOCATION: (1164)..(1256)
<223> OTHER INFORMATION: exon
<220> FEATURE:
<221> NAME/KEY: misc_feature
<222> LOCATION: (1257)..(1321)
<220> FEATURE:
<221> NAME/KEY: misc_feature
<222> LOCATION: (1322)..(1478)
<220> FEATURE:
<221> NAME/KEY: misc_feature
<222> LOCATION: (1479)..(1543)
<220> FEATURE:
<221> NAME/KEY: misc_feature
<222> LOCATION: (1544)..(1720)
<220> FEATURE:
<221> NAME/KEY: misc_feature
<222> LOCATION: (1721)..(1793)
<220> FEATURE:
<221> NAME/KEY: misc_feature
<222> LOCATION: (1794)..(1956)
<223> OTHER INFORMATION: exon
<220> FEATURE:
<221> NAME/KEY: misc_feature
<222> LOCATION: (1957)..(2019)
<223> OTHER INFORMATION: Intron
<220> FEATURE:
<221> NAME/KEY: misc_feature
<222> LOCATION: (2020)..(2096)
<220> FEATURE:
<221> NAME/KEY: misc_feature
<222> LOCATION: (2097)..(2189)
<220> FEATURE:
<221> NAME/KEY: misc_feature
<222> LOCATION: (2190)..(2294)
<223> OTHER INFORMATION: exon
<220> FEATURE:
<221> NAME/KEY: misc_feature
<222> LOCATION: (2295)..(2368)
<220> FEATURE:
<221> NAME/KEY: misc_feature
<222> LOCATION: (2369)..(2755)
<220> FEATURE:
<221> NAME/KEY: misc_feature
<222> LOCATION: (2756)..(2808)
<220> FEATURE:
<221> NAME/KEY: misc_feature
<222> LOCATION: (2809)..(2917)
<220> FEATURE:
<221> NAME/KEY: misc_feature
<222> LOCATION: (2918)..(3003)
<220> FEATURE:
<221> NAME/KEY: misc_feature
<222> LOCATION: (3004)..(3215)
<220> FEATURE:
<221> NAME/KEY: misc_feature
<222> LOCATION: (3216)..(3310)
<220> FEATURE:
<221> NAME/KEY: misc_feature
<222> LOCATION: (3311)..(3520)
<220> FEATURE:
<221> NAME/KEY: misc_feature
<222> LOCATION: (3521)..(3587)
<220> FEATURE:
<221> NAME/KEY: misc_feature
<222> LOCATION: (3588)..(3608)

<400> SEQUENCE: 1
atgttcccag ctagactctc cctcgcggtt ctcttctcag tatcccctgc cctcgcatac      60
ttttctggct tagggcttgg ctccgaacgc agtatctttc gtcgcgacct aaattctact     120
ggagatgaat ccaacagcac tcaatggcca gcgcgtacgt tttctctggt taatgttaat     180
```

```
cgatccaggt ctgaccaaaa gttttttttc tatcgcagcg cttgctaatg gaggcaaatc      240
gtgggcttct gctttcaaaa aagcgaaagc gacagtcact gagatgaccg tggaagaatt      300
agccaacgtg cgtccagaga aaatcattcg tatgattatt ctcaacgagg gcaatcccag      360
atcacctcag gggttatagg tttgtgttca ggagtgacgg gtgctgtaac tcgacttgga      420
attcccgaat tttgtcttca agacggacct atcgggcctc gtggtgtgca tggaagttct      480
cagtttccag ctggtcttac cgttgctgcc acttgggacc ggacgctcat gtatgctcgt      540
gctagaggta tgggacaaga gttccatgat caaggcgtgc atcttgcagt gagttttttct     600 cccactcgta gtactccttg tagtaacttt ttcaccacta cctagttggc acctgtcact      660
ggcggtcgta agttcatgct taaactctgt aatgtgtttg gtgtctaatt caaatccagc      720
acttggtcgt acgcctttgt aagtcatgat cttcgaaaaa aagcgcacac tgatctgaag      780
cataatatcc aaaggaacgg aagaggctgg gaagggactt ttgctgatcc ttatgcttgt      840
ggcgaagctt cttacctatc tgtaaaaggc ttgaccgatg ctggcgtagc cacggtctca      900
aagcacgtat gagcaattc ctgttccttt cgccaagccg ttcttgataa tgtttgttcc       960
agtggatagc atatgaacag gaaacatcga gaaatctcta tatcgacatc gacggaggcg      1020
agtaaattcc cctccccaat ttatggctcg ttatattcat tacattcaac aacaacagtt      1080
tcgcaagcgg atattcagtt gccgtgagtc tcatccatac ccttccggca cgatcgtgtc      1140
taactatatg ttgctattca cagaatttcc tccaacgtcg acgacttgac catgcacgaa      1200
ctatacatgt ggtcatttgc tgaagctgtt cgggctggaa cgaatcatat catgtgaatc      1260
tcattcggaa tatctatatc tcccaagttt ttcctaactc atcaatcata accttctaca      1320
ggtgttccta taccgtatc aacaacactc attcgtgtag caacgccaaa gggcttaatc       1380
aactcctcaa aactgaactg aacttccagg gaggtgtagt cagtgactgg ggaggacaat      1440
gggacagtgt accggctgca gagaatggtt tggatgtggt gagttgttta gtcggaatcg      1500
gtattttatg tcgtgctaag tatgccaaaa ctctcacgat taggctatgc ctggaaaagg      1560
atttctggga gcgctgggag atttctgggg cgcaacattg gttgaattga tcaacaacgg      1620
cacagtcagc gaagatctcg ttcgagacaa agcagttcgc atcctgactg gtactatta      1680 cctcggtcaa gatactaatc caccaccacc ctttgtttat gtgagcaccc acttactaac      1740
cacttcgaat ttatcgatct catcgtactc aatatcgtgt cggtggtaaa cagaacacaa      1800
tcggagcgcc tactttgaat gctacttctg ggtatcgaaa cgttcggaaa ccagggaccg      1860
cggagctgat aaaggaaatc ggaagcgcga gcgttactct cctgaagaac accggtagtc      1920 taccettgaa acaccegcag cggattgcag tattgggtac gttgaatctt cggacttcac      1980
tttgtttcca taaatatact cactcatttg gtccataagg caacgatgct acttataacg      2040
tgctcggtcc caatgcttgt ggtttggcaa acagtgcctg tgatatcgac aaccttgtat      2100
gttttatctc attattcctc gtatcgtagc ttgcctttta tttataatcg ctttgattat      2160
tgacttgact gactttacta tggttttaga atggtacctt gacaacagga ggcggaagcg      2220
ggtcggcact ttcaccatac accatcactc ccctcgaagc gctgcagaaa agggcaatcg      2280
aagataacgc cgaggttcga tgactgaact taattagctc ttcttctcct caataataaa      2340
aacccatcac tcaacctctt ccgtttagat cgccgcagtc gtcgcaaaca gcaacaccac      2400
caccggcgca gaagacgcaa tcgccgcccc cctccctgac gccgacgtta cctttgtctt      2460
cctcaaccga tattccgagg aaggtgcaga tgcgcctgat ttttccctcg gaggcgacgg      2520
tgacaacctc atggatctcg ccgtcacgta ttcgtccaac gtcgtcgtcg tgatacacac      2580
```

-continued

| | |
|---|---|
| caccggtgtc gtggatattg aaaaatgggc ggataaccca aatgttacgg cgatcctcgt | 2640 |
| tgcgtatctc cctgggcaag aagctggaaa tagtctggtt ccggttttgt atggtgatgt | 2700 |
| tgcgccgagt gggaagcttc cgtggacttg ggggaagagt attgatgatt atgttgtaag | 2760 |
| ttttttcctt cggtttcctt tcttacggtg tttgattgtt gtatgtagcc taacggtgtt | 2820 |
| gtatacaccg atgcatactc tcctcaatca aattttacgg aaggtgtatt catcgattac | 2880 |
| cgctggttcg acaagatggg tataactcct cgatatggta acgtattcat acccctctac | 2940 |
| tctttattac cttatcatca tttctcaaac tttcttgtct tgtctcgcct tactctcatc | 3000 |
| cagaattcgg attcggtcta tcctacacaa ccttcacata ctcgaacttg atcgtcgatc | 3060 |
| acggtcggtg ggcgaaagat tactcgtctg taatggaaac agcggagcca ttcgctgaat | 3120 |
| gggacggcac caattcgctt tacgacgtga tattcactgt gttcgcgacc atcactaaca | 3180 |
| ctgggaacct tactgggagt gaagtcgctc aattggttcg ttcatttgcc acacaagttt | 3240 |
| tgcgctagct aacgtcgaaa atccctttt tttttgtttt tttctttgtt tttcacattc | 3300 |
| catttaaaag tacatctcca tcccaggaga caaccaaccc gtgcgtcaac tacgcggttt | 3360 |
| cgacaagatc aaagatttac ctgtcggtga ttctgctgtc gtcaccttcc caattcggcg | 3420 |
| caaggacgtc agctcgtggt ctgttgttga ccagttgtgg tatgtgccga atggagactt | 3480 |
| tttgatttct gtcgggggga gttctcggga tttgcctctt gtaagtcatc ctattatccc | 3540 |
| cctcctcgtt tcctggaagt taagtatcaa tgttgatgca tgtacagaac actacttgga | 3600 |
| cgccgtga | 3608 |

<210> SEQ ID NO 2
<211> LENGTH: 803
<212> TYPE: PRT
<213> ORGANISM: Lentinula edodes

<400> SEQUENCE: 2

Met Phe Pro Ala Arg Leu Ser Leu Ala Val Leu Phe Ser Val Ser Pro
1               5                   10                  15

Ala Leu Ala Tyr Phe Ser Gly Leu Gly Leu Gly Ser Glu Arg Ser Ile
            20                  25                  30

Phe Arg Arg Asp Leu Asn Ser Thr Gly Asp Glu Ser Asn Ser Thr Gln
        35                  40                  45

Trp Pro Ala Pro Leu Ala Asn Gly Gly Lys Ser Trp Ala Ser Ala Phe
    50                  55                  60

Lys Lys Ala Lys Ala Thr Val Thr Glu Met Thr Val Glu Glu Leu Ala
65                  70                  75                  80

Asn Ile Thr Ser Gly Val Ile Gly Leu Cys Ser Gly Val Thr Gly Ala
                85                  90                  95

Val Thr Arg Leu Gly Ile Pro Glu Phe Cys Leu Gln Asp Gly Pro Ile
            100                 105                 110

Gly Pro Arg Gly Val His Gly Ser Ser Gln Phe Pro Ala Gly Leu Thr
        115                 120                 125

Val Ala Ala Thr Trp Asp Arg Thr Leu Met Tyr Ala Arg Ala Arg Gly
    130                 135                 140

Met Gly Gln Glu Phe His Asp Gln Gly Val His Leu Ala Leu Ala Pro
145                 150                 155                 160

Val Thr Gly Gly Pro Leu Gly Arg Thr Pro Leu Asn Gly Arg Gly Trp
                165                 170                 175

Glu Gly Thr Phe Ala Asp Pro Tyr Ala Cys Gly Glu Ala Ser Tyr Leu
            180                 185                 190

```
Ser Val Lys Gly Leu Thr Asp Ala Gly Val Ala Thr Val Ser Lys His
        195                 200                 205
Trp Ile Ala Tyr Glu Gln Glu Thr Ser Arg Asn Leu Tyr Ile Asp Ile
        210                 215                 220
Asp Gly Val Ser Gln Ala Asp Ile Gln Leu Pro Ile Ser Ser Asn Val
225                 230                 235                 240
Asp Asp Leu Thr Met His Glu Leu Tyr Met Trp Ser Phe Ala Glu Ala
                245                 250                 255
Val Arg Ala Gly Thr Asn His Ile Met Cys Ser Tyr Asn Arg Ile Asn
                260                 265                 270
Asn Thr His Ser Cys Ser Asn Ala Lys Gly Leu Asn Gln Leu Leu Lys
                275                 280                 285
Thr Glu Leu Asn Phe Gln Gly Val Val Ser Asp Trp Gly Gly Gln
        290                 295                 300
Trp Asp Ser Val Pro Ala Ala Glu Asn Gly Leu Asp Val Ala Met Pro
305                 310                 315                 320
Gly Lys Gly Phe Leu Gly Ala Leu Gly Asp Phe Trp Gly Ala Thr Leu
                325                 330                 335
Val Glu Leu Ile Asn Asn Gly Thr Val Ser Glu Asp Leu Val Arg Asp
                340                 345                 350
Lys Ala Val Arg Ile Leu Thr Gly Tyr Tyr Tyr Leu Gly Gln Asp Thr
        355                 360                 365
Asn Pro Pro Pro Phe Val Tyr Asn Thr Ile Gly Ala Pro Thr Leu
        370                 375                 380
Asn Ala Thr Ser Gly Tyr Arg Asn Val Arg Lys Pro Gly Thr Ala Glu
385                 390                 395                 400
Leu Ile Lys Glu Ile Gly Ser Ala Ser Val Thr Leu Leu Lys Asn Thr
                405                 410                 415
Gly Ser Leu Pro Leu Lys His Pro Gln Arg Ile Ala Val Leu Gly Asn
                420                 425                 430
Asp Ala Thr Tyr Asn Val Leu Gly Pro Asn Ala Cys Gly Leu Ala Asn
        435                 440                 445
Ser Ala Cys Asp Ile Asp Asn Leu Asn Gly Thr Leu Thr Thr Gly Gly
        450                 455                 460
Gly Ser Gly Ser Ala Leu Ser Pro Tyr Thr Ile Thr Pro Leu Glu Ala
465                 470                 475                 480
Leu Gln Lys Arg Ala Ile Glu Asp Asn Ala Glu Ile Ala Ala Val Val
                485                 490                 495
Ala Asn Ser Asn Thr Thr Thr Gly Ala Glu Asp Ala Ile Ala Ala Leu
                500                 505                 510
Leu Pro Asp Ala Asp Val Thr Phe Val Phe Leu Asn Arg Tyr Ser Glu
        515                 520                 525
Glu Gly Ala Asp Ala Pro Asp Phe Ser Leu Gly Gly Asp Gly Asp Asn
        530                 535                 540
Leu Met Asp Leu Ala Val Thr Tyr Ser Ser Asn Val Val Val Ile
545                 550                 555                 560
His Thr Thr Gly Val Val Asp Ile Glu Lys Trp Ala Asp Asn Pro Asn
                565                 570                 575
Val Thr Ala Ile Leu Val Ala Tyr Leu Pro Gly Gln Glu Ala Gly Asn
                580                 585                 590
Ser Leu Val Pro Val Leu Tyr Gly Asp Val Ala Pro Ser Gly Lys Leu
        595                 600                 605
```

```
Pro Trp Thr Trp Gly Lys Ser Ile Asp Asp Tyr Val Pro Asn Gly Val
610                 615                 620

Val Tyr Thr Asp Ala Tyr Ser Pro Gln Ser Asn Phe Thr Glu Gly Val
625                 630                 635                 640

Phe Ile Asp Tyr Arg Trp Phe Asp Lys Met Gly Ile Thr Pro Arg Tyr
                645                 650                 655

Glu Phe Gly Phe Gly Leu Ser Tyr Thr Thr Phe Thr Tyr Ser Asn Leu
            660                 665                 670

Ile Val Asp His Gly Arg Trp Ala Lys Asp Tyr Ser Ser Val Met Glu
            675                 680                 685

Thr Ala Glu Pro Phe Ala Glu Trp Asp Gly Thr Asn Ser Leu Tyr Asp
690                 695                 700

Val Ile Phe Thr Val Phe Ala Thr Ile Thr Asn Thr Gly Asn Leu Thr
705                 710                 715                 720

Gly Ser Glu Val Ala Gln Leu Tyr Ile Ser Ile Pro Gly Asp Asn Gln
                725                 730                 735

Pro Val Arg Gln Leu Arg Gly Phe Asp Lys Ile Lys Asp Leu Pro Val
                740                 745                 750

Gly Asp Ser Ala Val Val Thr Phe Pro Ile Arg Arg Lys Asp Val Ser
                755                 760                 765

Ser Trp Ser Val Val Asp Gln Leu Trp Tyr Val Pro Asn Gly Asp Phe
                770                 775                 780

Leu Ile Ser Val Gly Gly Ser Ser Arg Asp Leu Pro Leu Asn Thr Thr
785                 790                 795                 800

Trp Thr Pro
```

<210> SEQ ID NO 3
<211> LENGTH: 2412
<212> TYPE: DNA
<213> ORGANISM: Lentinula edodes

<400> SEQUENCE: 3

```
atgttcccag ctagactctc cctcgcggtt ctcttctcag tatcccctgc cctcgcatac      60
ttttctggct tagggcttgg ctccgaacgc agtatctttc gtcgcgacct aaattctact     120
ggagatgaat ccaacagcac tcaatggcca gcgccgcttg ctaatggagg caaatcgtgg     180
gcttctgctt tcaaaaaagc gaaagcgaca gtcactgaga tgaccgtgga agaattagcc     240
aacatcacct caggggttat aggtttgtgt tcaggagtga cgggtgctgt aactcgactt     300
ggaattcccg aattttgtct tcaagacgga ccctatcggg ctcgtggtgt gcatggaagt     360
tctcagtttc cagctggtct taccgttgct gccacttggg accggacgct catgtatgct     420
cgtgctagag gtatgggaca agagttccat gatcaaggcg tgcatcttgc attggcacct     480
gtcactggcg gtccacttgg tcgtacgcct ttgaacggaa gaggctggga agggactttt     540
gctgatcctt atgcttgtgg cgaagcttct tacctatctg taaaaggctt gaccgatgct     600
ggcgtagcca cggtctcaaa gcactggata gcatatgaac aggaaacatc gagaaatctc     660
tatatcgaca tcgacggagt ttcgcaagcg atattcagt tgccaatttc ctccaacgtc     720
gacgacttga ccatgcacga actatacatg tggtcatttg ctgaagctgt tcgggctgga     780
acgaatcata tcatgtgttc ctataaccgt atcaacaaca ctcattcgtg tagcaacgcc     840
aaagggctta atcaactcct caaaactgaa ctgaacttcc agggaggtgt agtcagtgac     900
tggggaggac aatgggacag tgtaccggct gcagagaatg gtttggatgt ggctatgcct     960
ggaaaaggat ttctgggagc gctgggagat ttctggggcg caacattggt tgaattgatc    1020
```

```
aacaacggca cagtcagcga agatctcgtt cgagacaaag cagttcgcat cctgactggg   1080
tactattacc tcggtcaaga tactaatcca ccaccaccct tgtttataa cacaatcgga    1140 gcgcctactt tgaatgctac ttctgggtat cgaaacgttc ggaaaccagg gaccgcggag   1200
ctgataaagg aaatcggaag cgcgagcgtt actctcctga agaacaccgg tagtctaccc   1260
ttgaaacacc cgcagcggat tgcagtattg ggcaacgatg ctacttataa cgtgctcggt   1320
cccaatgctt gtggtttggc aaacagtgcc tgtgatatcg acaaccttaa tggtaccttg   1380
acaacaggag gcggaagcgg gtcggcactt tcaccataca ccatcactcc cctcgaagcg   1440
ctgcagaaaa gggcaatcga agataacgcc gagatcgccg cagtcgtcgc aaacagcaac   1500
accaccaccg gcgcagaaga cgcaatcgcc gccctcctcc ctgacgccga cgttacctt    1560 gtcttcctca accgatattc cgaggaaggt gcagatgcgc ctgatttttc cctcggaggc   1620
gacggtgaca acctcatgga tctcgccgtc acgtattcgt ccaacgtcgt cgtcgtgata   1680
cacaccaccg gtgtcgtgga tattgaaaaa tgggcggata acccaaatgt tacgccgatc   1740
ctcgttgcgt atctccctgg gcaagaagct ggaaatagtc tggttccggt tttgtatggt   1800
gatgttgcgc cgagtgggaa gcttccgtgg acttggggga agagtattga tgattatgtt   1860
cctaacggtg ttgtatacac cgatgcatac tctcctcaat caaatttac ggaaggtgta    1920 ttcatcgatt accgctggtt cgacaagatg ggtataactc ctcgatatga attcggattc   1980
ggtctatcct acacaacctt cacatactcg aacttgatcg tcgatcacgg tcggtgggcg   2040
aaagattact cgtctgtaat ggaaacagcg gagccattcg ctgaatggga cggcaccaat   2100
tcgctttacg acgtgatatt cactgtgttc gcgaccatca ctaacactgg gaaccttact   2160
gggagtgaag tcgctcaatt gtacatctcc atcccaggag acaaccaacc cgtgcgtcaa   2220
ctacgcggtt tcgacaagat caaagattta cctgtcggtg attctgctgt cgtcaccttc   2280
ccaattcggc gcaaggacgt cagctcgtgg tctgttgttg accagttgtg gtatgtgccg   2340
aatggagact ttttgatttc tgtcgggggg agttctcggg atttgcctct taacactact   2400
tggacgccgt ga                                                        2412
```

```
<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Leu Pro Trp Thr Trp Gly Lys
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Gln Ser Gly Ser Leu Pro Leu Gln His Pro Gln Arg
1               5                   10

<210> SEQ ID NO 6
<211> LENGTH: 11
<212> TYPE: PRT
<213> ORGANISM: Artificial Sequence
```

```
<220> FEATURE:
<223> OTHER INFORMATION: Synthetic Peptide

<400> SEQUENCE: 6

His Trp Leu Ala Tyr Glu Gln Glu Thr Ser Arg
1               5                   10

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
cttgcgtacg agcargarac                                                  20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
cactggcttg cgtaygarca                                                  20

<210> SEQ ID NO 9
<211> LENGTH: 16
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (12)..(12)
<223> OTHER INFORMATION: n is a, c, g, or t

<400> SEQUENCE: 9
ccctggcttg cntayg                                                      16

<210> SEQ ID NO 10
<211> LENGTH: 21
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 10
agcctccagt ggcgtnagng t                                                21

<210> SEQ ID NO 11
<211> LENGTH: 21
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (16)..(16)
<223> OTHER INFORMATION: n is a, c, g, or t
```

```
<220> FEATURE:
<221> NAME/KEY: misc_feature
<222> LOCATION: (19)..(19)
<223> OTHER INFORMATION: n is a, c, g, or t

<400> SEQUENCE: 11
ctgcagagcc tccagnggng t                                                    21

<210> SEQ ID NO 12
<211> LENGTH: 20
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 12
ttctgcagag cctcnagngg                                                      20

<210> SEQ ID NO 13
<211> LENGTH: 21
<212> TYPE: DNA
<213> ORGANISM: Artificial Sequence
<220> FEATURE:
<223> OTHER INFORMATION: oligonucleotide

<400> SEQUENCE: 13
gactggttcc aattgacaag c                                                    21

<210> SEQ ID NO 14
<211> LENGTH: 22
<212> TYPE: DNA
<213> ORGANISM: Artificial Sequence
<220> FEATURE:
<223> OTHER INFORMATION: oligonucleotide

<400> SEQUENCE: 14
ggcaaatggc attctgacat cc                                                   22

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Asp Leu Pro Val Gly Asp Ser Ala Val Val Thr Tyr Pro Pro Arg
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 16

Thr Leu Thr Pro Leu Glu Ala Leu Gln Lys
1               5                   10
```